(12) United States Patent
Bar-Tal et al.

(10) Patent No.: US 8,478,383 B2
(45) Date of Patent: Jul. 2, 2013

(54) PROBE TRACKING USING MULTIPLE TRACKING METHODS

(75) Inventors: Meir Bar-Tal, Haifa (IL); Daniel Osadchy, Haifa (IL)

(73) Assignee: Biosense Webster (Israel), Ltd., Yokneam (IL)

( * ) Notice: Subject to any disclaimer, the term of this patent is extended or adjusted under 35 U.S.C. 154(b) by 110 days.

(21) Appl. No.: 12/967,439

(22) Filed: Dec. 14, 2010

(65) Prior Publication Data

US 2012/0150022 A1 Jun. 14, 2012

(51) Int. Cl.
*A61B 5/00* (2006.01)

(52) U.S. Cl.
USPC ............... 600/424; 700/302; 702/95; 703/7

(58) Field of Classification Search
USPC ............... 600/424; 700/56, 57, 302; 702/84, 702/94, 95, 189–199; 703/2, 7, 11
See application file for complete search history.

(56) References Cited

U.S. PATENT DOCUMENTS

| | | | |
|---|---|---|---|
| 5,899,860 A | 5/1999 | Pfeiffer et al. | |
| 5,983,126 A | 11/1999 | Wittkampf | |
| 6,432,041 B1 * | 8/2002 | Taniguchi et al. | 600/118 |
| 6,574,498 B1 | 6/2003 | Gilboa | |
| 7,277,834 B2 * | 10/2007 | Bar Tal et al. | 703/2 |
| 2005/0020911 A1 | 1/2005 | Viswanathan | |
| 2006/0173251 A1 | 8/2006 | Govari et al. | |
| 2007/0016007 A1 | 1/2007 | Govari et al. | |
| 2007/0038078 A1 | 2/2007 | Osadchy | |
| 2008/0033452 A1 | 2/2008 | Vetter | |
| 2010/0121151 A1 * | 5/2010 | Donhowe et al. | 600/141 |

FOREIGN PATENT DOCUMENTS

EP 2186474 B1 1/2012

OTHER PUBLICATIONS

EP Search Report Appln No. 11193164.8-2319 dated Mar. 14, 2012.

* cited by examiner

*Primary Examiner* — Parikha Mehta
(74) *Attorney, Agent, or Firm* — Louis J. Capezzuto

(57) ABSTRACT

A method, including: receiving an input indicative of respective apparent locations of a plurality of points disposed along a length of a probe inside a body of a subject, and applying a model of known mechanical properties of the probe to the respective apparent locations so as to minimize a first cost function with respect to shapes that can be assumed by the probe in the body. The method further includes choosing a shape responsively to the minimized first cost function and determining preliminary coordinates of the apparent locations responsively to the shape, minimizing a second cost function with respect to differences between the apparent locations and the preliminary coordinates, and generating corrected coordinates of the points along the length of the probe based on the minimized second cost function.

18 Claims, 11 Drawing Sheets

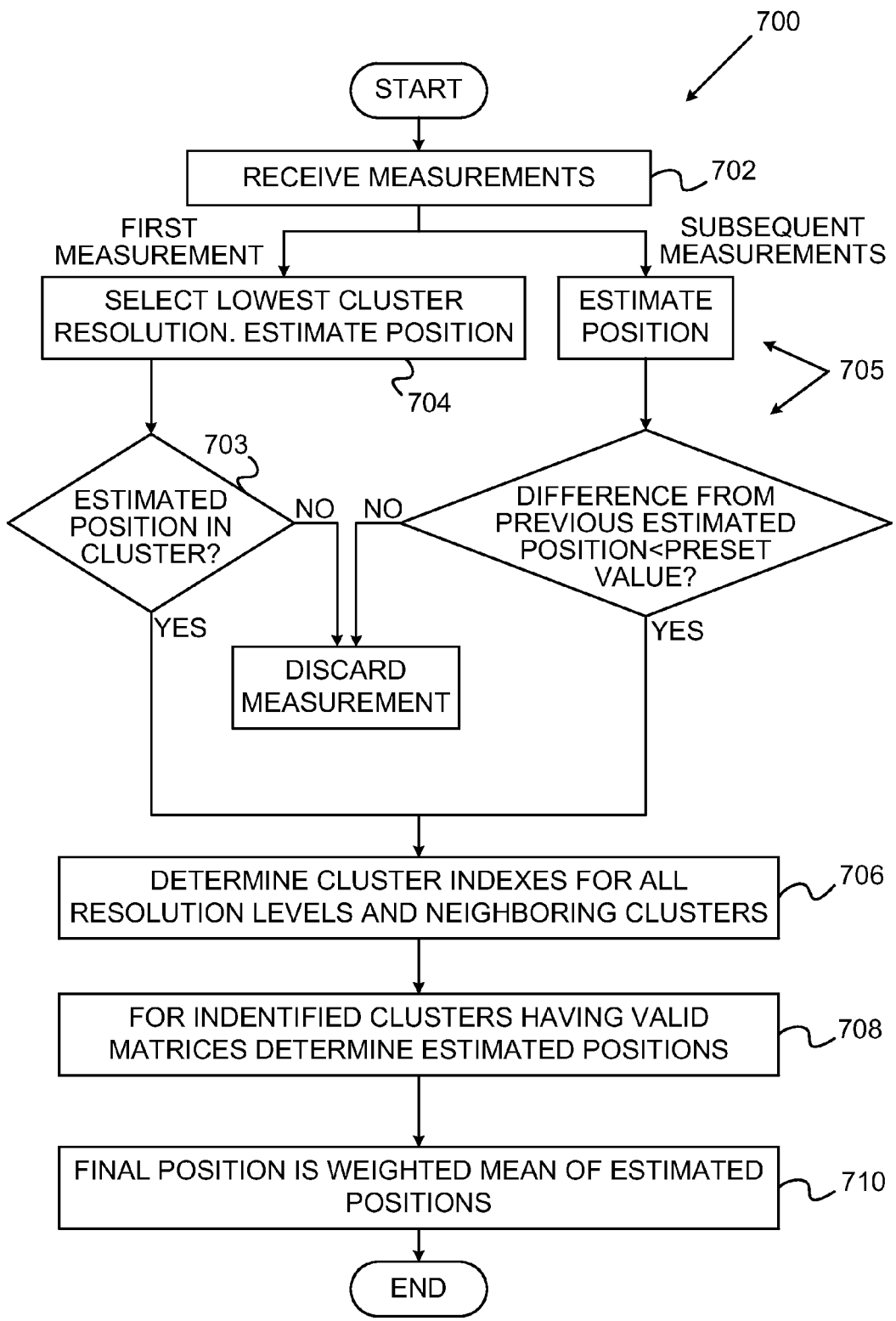

PROBE TRACKING USING MULTIPLE TRACKING METHODS

FIELD OF THE INVENTION

The present invention relates generally to sensing the position of an object placed within a living body, and specifically to position sensing of a probe in a living body using multiple measuring parameters.

BACKGROUND OF THE INVENTION

A wide range of medical procedures involve placing objects, such as sensors, tubes, catheters, dispensing devices, and implants, within the body. Real-time imaging methods are often used to assist doctors in visualizing the object and its surroundings during these procedures. In most situations, however, real-time three-dimensional imaging is not possible or desirable. Instead, systems for obtaining real-time spatial coordinates of the internal object are often utilized.

U.S. Patent Application 2007/0016007, to Govari et al., whose disclosure is incorporated herein by reference, describes a hybrid magnetic-based and impedance-based position sensing system. The system includes a probe adapted to be introduced into a body cavity of a subject.

U.S. Pat. No. 6,574,498, to Gilboa, whose disclosure is incorporated herein by reference, describes a system for determining the position of a work piece within a cavity of an opaque body. The system claims to use a transducer that interacts with a primary field, and several transducers that interact with a secondary field.

U.S. Pat. No. 5,899,860, to Pfeiffer, et al., whose disclosure is incorporated herein by reference, describes a system for determining the position of a catheter inside the body of a patient. A correction function is determined from the difference between calibration positions derived from received location signals and known, true calibration positions, whereupon catheter positions, derived from received position signals, are corrected in subsequent measurement stages according to the correction function.

U.S. Pat. No. 5,983,126, to Wittkampf, whose disclosure is incorporated herein by reference, describes a system in which catheter position is detected using electrical impedance methods.

U.S. Patent Application Publications 2006/0173251, to Govari et al., and 2007/0038078, to Osadchy, whose disclosures are incorporated herein by reference, describe methods for sensing the position of a probe by passing electrical currents through the body between an electrode on the probe and a plurality of locations on a surface of the body. These methods likewise use the electrical impedance of the body in sensing probe position.

The description above is presented as a general overview of related art in this field and should not be construed as an admission that any of the information it contains constitutes prior art against the present patent application.

SUMMARY OF THE INVENTION

An embodiment of the present invention provides a method, including:

receiving an input indicative of respective apparent locations of a plurality of points disposed along a length of a probe inside a body of a subject;

applying a model of known mechanical properties of the probe to the respective apparent locations so as to minimize a first cost function with respect to shapes that can be assumed by the probe in the body;

choosing a shape responsively to the minimized first cost function and determining preliminary coordinates of the apparent locations responsively to the shape;

minimizing a second cost function with respect to differences between the apparent locations and the preliminary coordinates; and generating corrected coordinates of the points along the length of the probe based on the minimized second cost function.

Typically, receiving the input includes receiving inputs from position transducers disposed along the length of the probe, and each of the plurality of points corresponds to a respective location of a position transducer. The position transducer may be selected from a group consisting of an impedance measurement electrode, a single-axis magnetic sensor, a three-axis magnetic sensor, and an ultrasonic sensor.

In one embodiment the plurality of points includes a respective plurality of investigation-electrodes disposed along the length of the probe, and receiving the input indicative of the respective apparent locations includes:

positioning body-electrodes in galvanic contact with the body of the subject;

positioning a mapping-tool, having a mapping-electrode, in the body of the subject;

generating a set of calibration-currents between the body-electrodes and the mapping-electrode at different positions in the body;

deriving a relation between the set of the calibration-currents and the different positions;

generating respective sets of investigation-tool-currents between the body-electrodes and the plurality of investigation-electrodes; and determining the respective apparent locations in response to the relation and the set of investigation-tool-currents.

Typically, positioning the mapping-tool includes tracking the mapping-tool at the different positions using a location-measuring system. Alternatively or additionally, positioning the mapping-tool includes positioning the mapping-tool in a plurality of regions in the body, and deriving the relation includes determining for each region a respective different region-relation between the set of the calibration-currents and the different positions.

In a disclosed embodiment the method further includes applying an adjustment parameter to the preliminary coordinates to formulate parameterized preliminary coordinates, minimizing the second cost function includes computing differences between the apparent locations and the parameterized preliminary coordinates so as to determine a value of the adjustment parameter, and generating the corrected coordinates includes applying the value of the adjustment parameter to the preliminary coordinates to evaluate the parameterized corrected coordinates.

There is further provided, according to an embodiment of the present invention, apparatus, including:

a probe having a plurality of points disposed along a length thereof; and a processor which is configured to:

receive an input indicative of respective apparent locations of the plurality of the points inside a body of a subject, apply a model of known mechanical properties of the probe to the respective apparent locations so as to minimize a first cost function with respect to shapes that can be assumed by the probe in the body, choose a shape responsively to the minimized first cost function and determine preliminary coordinates of the apparent locations responsively to the shape, minimize a second cost function with respect to differences between the apparent locations and the preliminary coordinates, and generate corrected coordinates of the points along the length of the probe based on the minimized second cost function.

There is further provided, according to an embodiment of the present invention, a computer software product including a non-transitory computer-readable medium having computer program instructions recorded therein, which instructions, when read by a computer, cause the computer to:

receive an input indicative of respective apparent locations of a plurality of points disposed along a length of a probe inside a body of a subject, apply a model of known mechanical properties of the probe to the respective apparent locations so as to minimize a first cost function with respect to shapes that can be assumed by the probe in the body;

choose a shape responsively to the minimized first cost function and determining preliminary coordinates of the apparent locations responsively to the shape;

minimize a second cost function with respect to differences between the apparent locations and the preliminary coordinates; and generate corrected coordinates of the points along the length of the probe based on the minimized second cost function.

The present disclosure will be more fully understood from the following detailed description of the embodiments thereof, taken together with the drawings, in which:

BRIEF DESCRIPTION OF THE DRAWINGS

FIG. 9 is a flowchart showing steps 46 to generate catheter positions using the matrices generated by the flowchart of FIG. 8, according to an embodiment of the present invention.

DETAILED DESCRIPTION OF EMBODIMENTS

OVERVIEW

In embodiments of the present invention, a first tracking sub-system is calibrated using a second, more accurate, tracking sub-system. Either sub-system may be used for measurement of the location and orientation of a probe, herein by way of example assumed to be a catheter tip, within the body of a patient. Both sub-systems are operated in a calibration phase, but only the first sub-system is used in a tracking phase.

The first sub-system generates currents between an electrode on the catheter tip and a number of conducting elements positioned on or within the body, so forming a current distribution. The location of the electrode is calculated from the current distribution. The second sub-system may be any location tracking system that operates on a different principle to that of the first sub-system. In the calibration phase, relations are formed between the results of the two sub-systems.

In the tracking phase, i.e., when the first sub-system is used by itself to track a probe, the relations are applied to the currents generated in the first sub-system. Applying the relations enhances the accuracy of the measurements of the position of electrodes on the probe, giving enhanced position values for the electrodes.

To further enhance the accuracy of the measurements made in the tracking phase, a mechanical model of the probe is applied to the results from the first sub-system. The mechanical model generates predictions of the positions of the electrodes. A cost function is formulated relating the two sets of positions, i.e. those from the first sub-system and those from the mechanical model, and the cost function is minimized to determine improved position values for the electrodes.

To further improve the determination of the positions of the electrodes, the two sets of position values are separately parameterized with an adjustment parameter. An optimal value for the adjustment parameter is determined by analyzing the two sets of parameterized position values, and the optimal value of the adjustment parameter is applied to the improved position values.

System Description

Figure 1A:
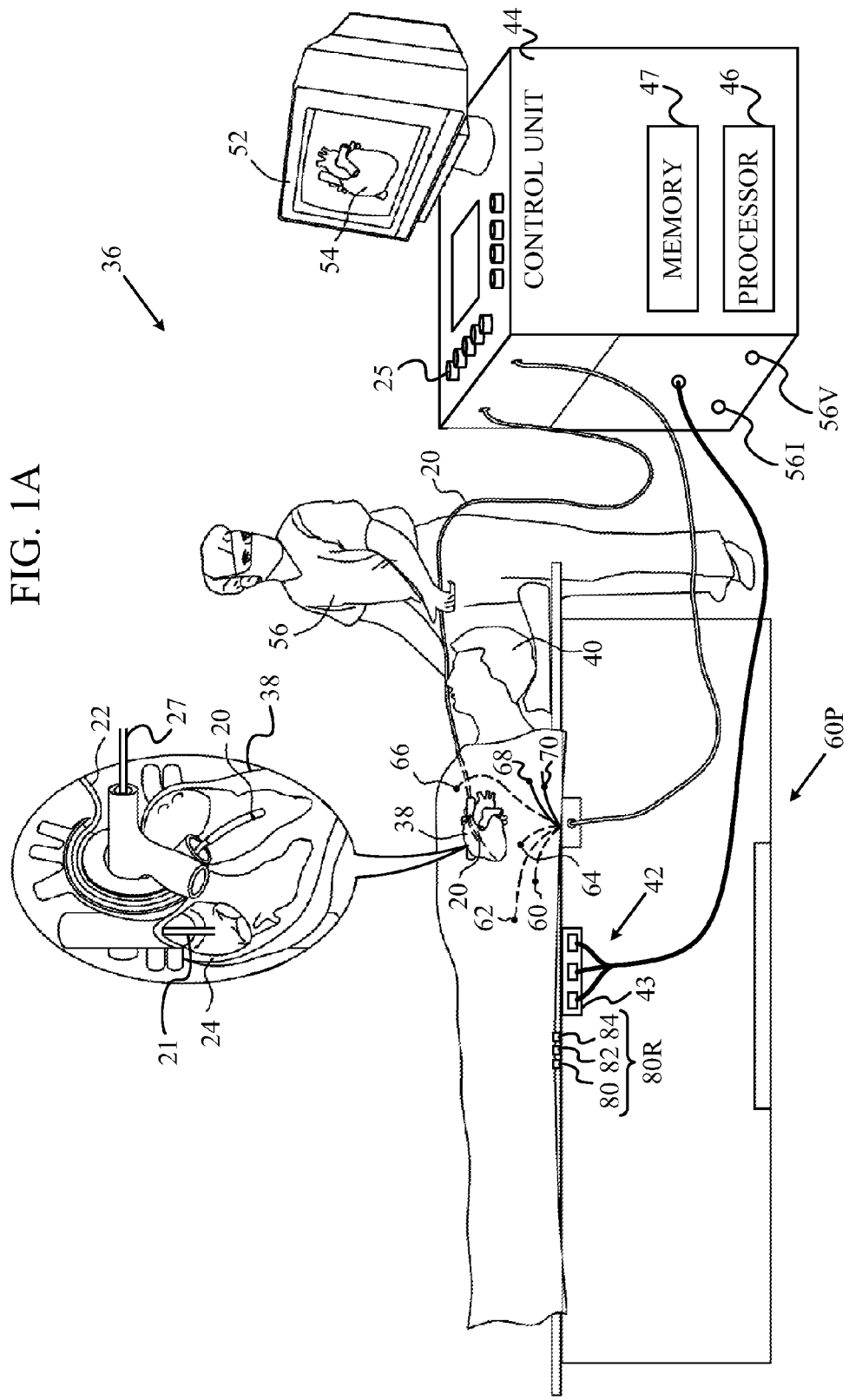
FIG. 1A is a schematic, pictorial illustration of a position sensing system, utilizing a hybrid catheter.
Figure 1B:
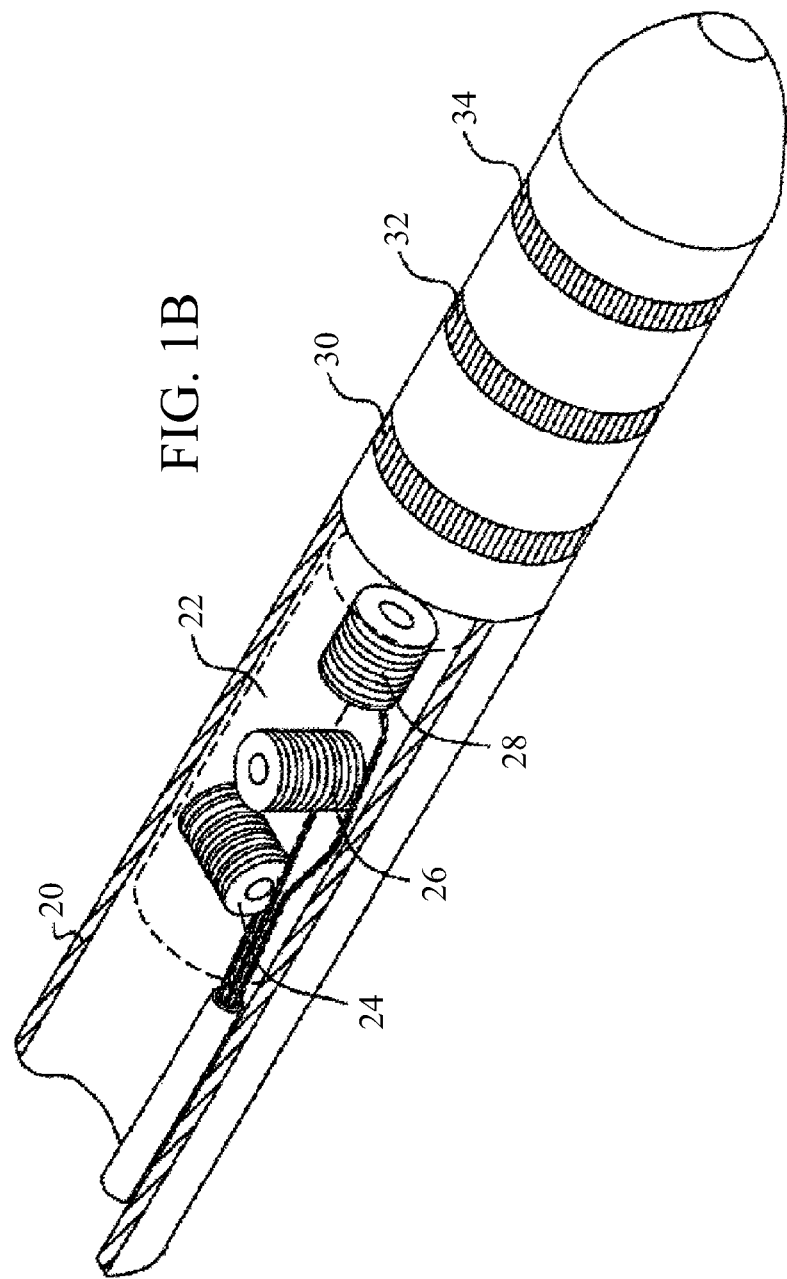
FIG. 1B is a schematic detailed view showing the distal end of the hybrid catheter, according to an embodiment of the present invention.

FIG. 1A is a schematic, pictorial illustration of a position sensing system 36, utilizing a hybrid catheter 20, and FIG. 1B is a schematic detailed view showing the distal end of the hybrid catheter, according to an embodiment of the present invention. The hybrid catheter acts as a probe in a medical procedure, and may also be referred to herein as a mapping-catheter. A medical professional 56 is assumed to operate system 36.

By way of example, except where otherwise stated in the description hereinbelow, mapping-catheter 20 is assumed to be used in an invasive procedure within a chamber of a heart 38 of a subject 40. Alternatively, position sensing system 36 may be used with probes similar to catheter 20 in other body cavities. Subject 40 is placed in a magnetic field generated, for example, by positioning under the subject a location pad 43 containing magnetic field generator coils 42. The magnetic fields generated by coils 42 generate electrical signals in coils 24, 26 and 28 of an electromagnetic (EM) sensor 22 located at the distal end of catheter 20. The electrical signals are conveyed to a control unit 44, which analyzes the signals so as to determine the coordinates of the position and of the orientation of catheter 20. Alternatively, the coils in magnetic field sensor 22 may be driven to generate magnetic fields, which are detected by coils 42.

Control unit 44 includes a processor 46, typically a computer with appropriate signal processing circuits. The processor uses a memory 47, which typically comprises both volatile and non-volatile data storage devices, wherein data for operating system 36 is stored. The processor is coupled to drive a console 52, which may provide a visual display 54 of the location of catheter 20.

Control unit 44 comprises alternating current drivers 561 which processor 46 uses to supply currents to mapping-catheter-conductive-electrodes 30, 32, and 34 that are located at the distal end of mapping-catheter 20. Processor 46 sets the alternating frequency of the current supplied to each electrode of catheter 20 to be different. The catheter electrodes are connected by wires through the insertion tube of the catheter to current and voltage measurement circuitry in control unit 44.

The control unit is connected by wires to body surface electrodes, also referred to herein as body-electrodes, which may be any type of body electrodes known in the art, such as button electrodes, needle electrodes, subcutaneous probes, or patch electrodes. The body-electrodes are typically in galvanic contact with the body surface of subject 40, and receive body surface currents therefrom. Where the following description refers to patch electrodes or patches, it will be understood that embodiments of the present invention may use any of the other type of electrodes described above.

In some embodiments, one or more of the body-electrodes may be positioned in galvanic contact with, and inside, the body of subject 40. Typically, control unit 44 tracks the position of these internally located body-electrodes, for example by these body-electrodes being configured to have tracking coils similar to coils 24, 26 and 28 in catheter 20. Except where otherwise stated, the following description assumes, for simplicity, that the body-electrodes are located on the body of subject 40. Those having ordinary skill in the art will be able to adapt the description, mutatis mutandis, to cover body-electrodes positioned inside the body of subject 40.

By way of example, body surface electrodes are herein assumed to comprise adhesive skin patches 60, 62, 64, 66, 68 and 70, generically referred to herein as active current location (ACL) patches 60P, or by an ACL patch index "i," where i is an integer between 1 and 6. ACL patches 60P may be placed at any convenient locations on the body surface of subject 40 in the vicinity of the probe. ACL patches 60P typically have respective associated tracking coils, similar to coils 24, 26 and 28 in catheter 20. In alternative embodiments of the invention, the body surface electrodes may vary in number. The body surface electrodes receive differing mapping-currents from the electrodes of the mapping-catheter, and the differing currents are analyzed to determine a location or position of catheter 20. Catheter thus comprises two components for measuring its location, one component operating in an EM sub-system of system 36, the other component operating in an ACL sub-system of the system 36.

Control unit 44 also comprises voltage generators 56V, which are connected to ACL patches "i" by their connecting wires, and which processor 46 uses to measure the impedance of the ACL patches.

The currents from drivers 561 and generators 56V are differentiated by processor 46 operating the currents and voltages at different frequencies. Thus there are six unique frequencies for the generators supplying voltage to the ACL patches, and a multiplicity of other unique frequencies for the drivers supplying current to the catheters.

In system 36 there may be one or more other hybrid catheters, generally similar to catheter 20, which are tracked by the system generally as catheter 20 is tracked. For clarity, in FIG. 1A the other catheters are not shown. In addition, in system 36 there may be other non-hybrid catheters comprising one or more electrodes, similar to electrodes 30, 32, and 34, but not comprising a sensor such as sensor 22. Non-hybrid catheters are probes which are herein also referred to as investigation-catheters, and the electrodes of the investigation-catheters are also referred to as investigation-catheter-conductive electrodes. As is described below, the investigation-catheter-conductive electrodes operate as impedance measurement electrodes, and also act as position transducers, so that system 36 is able to track these investigation-catheters. By way of example, one such non-hybrid catheter 21 is shown in FIG. 1A.

In one embodiment there are approximately 90 frequencies for current drivers 561, so that up to 90 catheter electrodes may be tracked simultaneously in system 36.

Skin patches, herein assumed by way of example to comprise three adhesive skin patches 80, 82, and 84, are typically placed on the back of subject 40 for use as position references. Patches 80, 82, and 84 are herein referred to generically as reference patches 80R. Each reference patch 80R has an EM sensor, which is generally similar to sensor 22, and which provides the position of its respective patch to processor 46. Reference patches 80R are connected to control unit 44 by wires.

System 36 may also include a reference position sensor, such as an internally-placed catheter, inserted into a moving organ of body 40, herein assumed to be heart 38, and maintained in a substantially fixed position relative to the moving organ. Herein the reference sensor is assumed to comprise a coronary sinus reference catheter (CSRC) 27, and is also referred to herein as reference catheter 27. Catheter 27 is typically a hybrid catheter. By comparing the position of catheter 20 to that of reference catheter 27, the coordinates of catheter 20 are accurately determined relative to the heart, irrespective of heart motion.

Typically, system 36 includes other elements and/or systems, which are not shown in the figures for the sake of simplicity, and which are referred to as necessary in the following description. For example, system 36 may include an ECG monitor (coupled to receive signals from one or more body surface electrodes, so as to provide an ECG synchronization signal to control unit 44), and/or an ablation system.

The configuration of FIG. 1A is an example configuration, which is chosen purely for the sake of conceptual clarity. In alternative embodiments, any other suitable configuration can also be used.

For example, the methods described hereinbelow may be applied in correcting position measurements made using position transducers of types other than electrodes, such as magnetic or ultrasonic position sensors. The term "position transducer" as used herein refers to an element mounted on the probe which causes control unit 44 to receive signals indicative of the coordinates of the element. The position transducer may thus comprise a receiver on the probe, which generates a position signal to the control unit based on energy received by the transducer; or it may comprise a transmitter, emitting energy that is sensed by a receiver external to the probe. Furthermore, the methods described hereinbelow may similarly be applied in visualizing the locations not only of catheters, but also of probes of other types, both in the heart and in other body organs and regions.

The flowcharts and block diagrams in the Figures illustrate the architecture, functionality, and operation of possible implementations of systems, methods and computer program products according to various embodiments of the present invention. In this regard, each block in the flowcharts or block diagrams may represent a module, segment, or portion of code, which comprises one or more executable instructions for implementing the specified logical function(s).

It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or by combinations of special purpose hardware and computer instructions.

Typically, processor 46 comprises a general-purpose processor, which is programmed to have instructions in software for carrying out the functions described herein. The software may be downloaded to the processor in electronic form, over a network, for example, or it may, alternatively or additionally, be provided and/or stored on non-transitory computer-readable tangible media, such as magnetic, optical, or electronic memory.

Figure 2A:
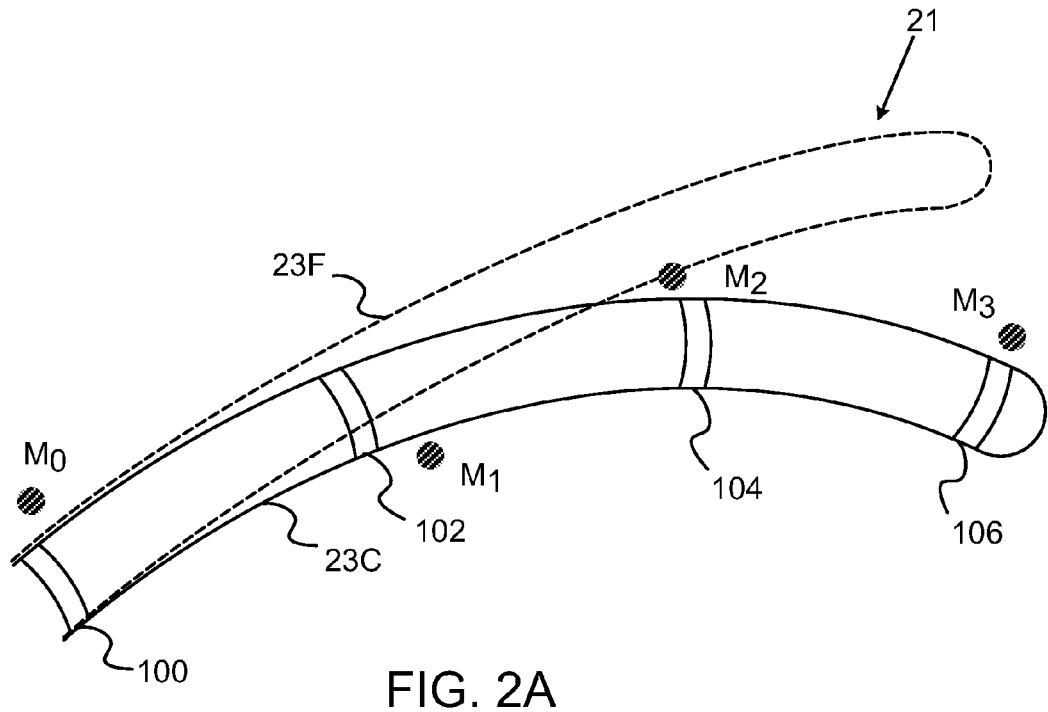
FIGS. 2A and 2B are diagrams that schematically show a non-hybrid catheter deviating from its free shape, according to an embodiment of the present invention.
Figure 2B:
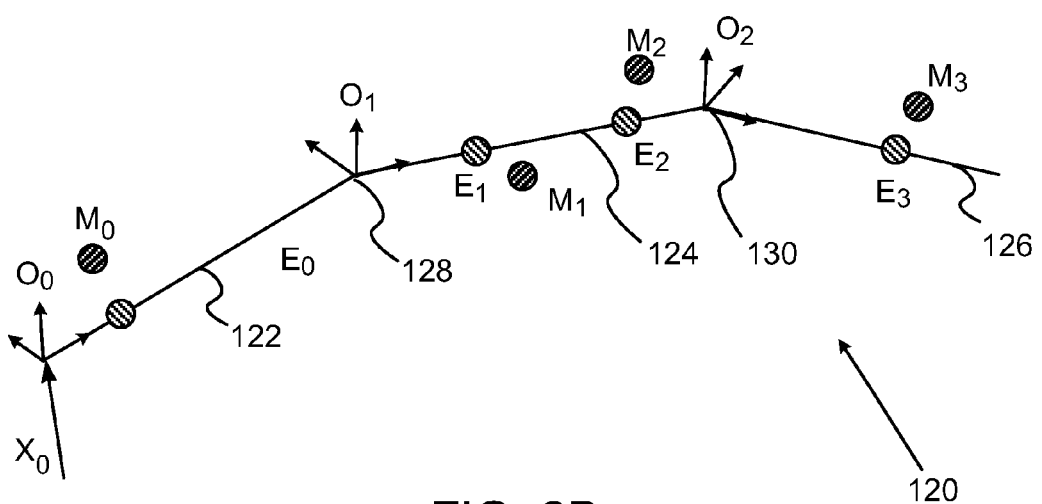

FIGS. 2A and 2B are diagrams that schematically show non-hybrid catheter 21 deviating from its free shape 23F, according to an embodiment of the present invention. FIG. 2A shows an actual shape 23C of catheter 21 in heart 38, the catheter having electrodes 100, 102, 104, 106. As described below, the locations of the electrodes of catheter 21 are derived, based on measuring currents passing between the electrodes and patches 60P. The measured locations of electrodes 100, 102, 104, 106, are respectively represented by points $M_0, M_1, M_2, M_3$. FIG. 2B is a diagram of a geometrical model 120 of catheter 21. Model 120 comprises straight rigid sections 122, 124 and 126, connected by joints 128 and 130 that allow rotation (bending and twisting). The position of the start of section 122 is described by a position vector $x_0$, and the orientation of section 122 is given by an orientation matrix $O_0$. Section 124 starts at the end of section 122 (i.e., at connecting joint 128), and its orientation is given by a matrix $O_1$. Section 126 starts at the end of section 124 (i.e., at connecting joint 130), and its orientation is given by a matrix $O_2$. Vector $x_0$ and matrices $O_0, O_1, O_2$, describe the actual state, i.e., the shape, of the model of the probe, wherein external forces cause the model to deviate from a free state in which no external forces are applied to the model. Although model 120 comprises three sections, alternative model geometries may comprise either fewer than three or more than three sections.

In model 120, points $E_0, E_1, E_2, E_3$, represent locations of electrodes 100, 102, 104, 106 that have been calculated in accordance with the model, i.e., that lie on the model. The calculated locations are based on the measured locations of points $M_0, M_1, M_2, M_3$ and on the relationship between these measured locations and mechanical properties assigned to the model. As described in more detail below, cost functions based on the mechanical properties of the probe are constructed. The cost functions are minimized to find the best match between the points $E_0, E_1, E_2, E_3$, and the measurements $M_0, M_1, M_2, M_3$.

Figure 3A:
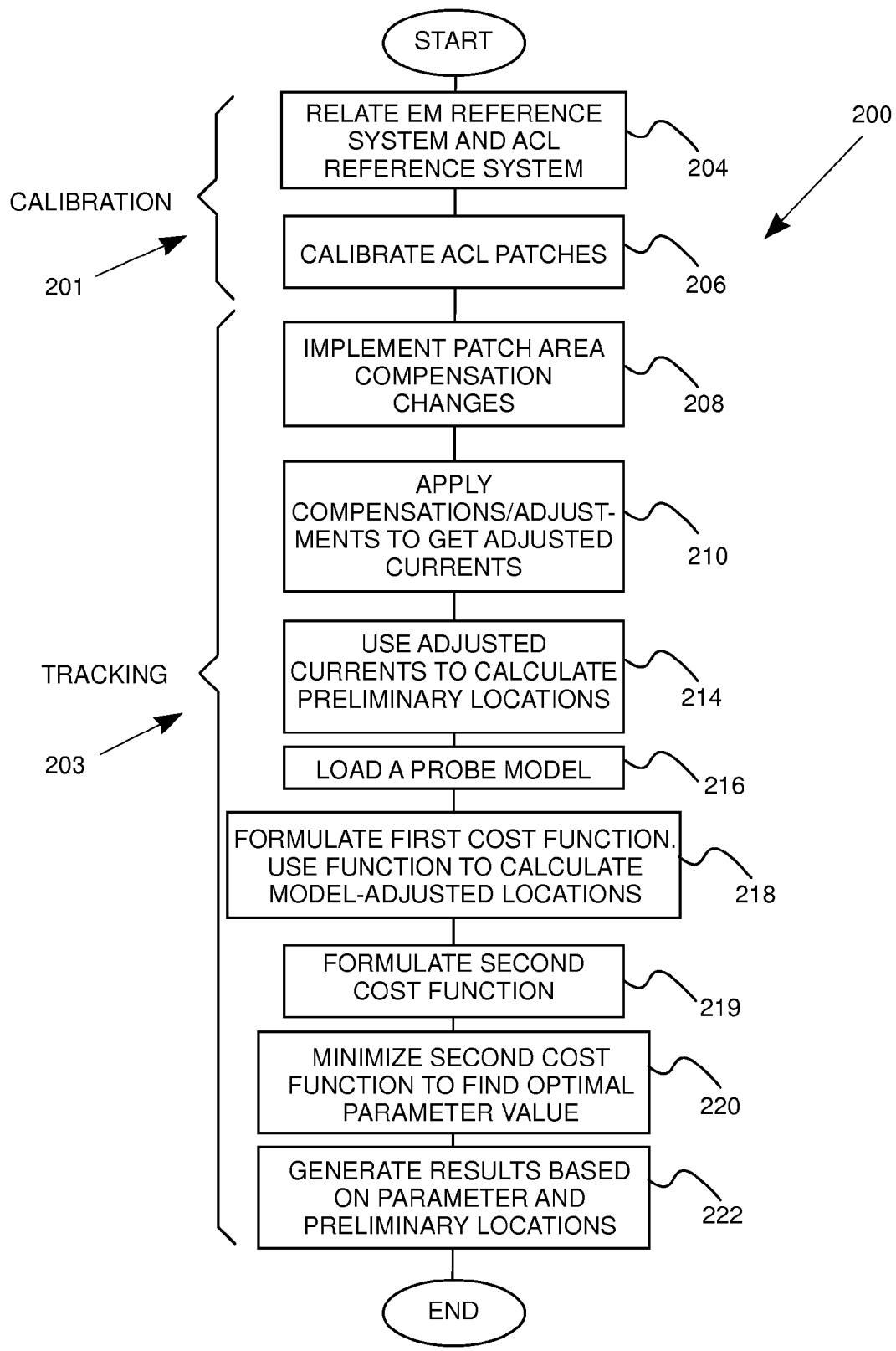
FIG. 3A is a flow chart schematically illustrating a process for operating the position sensing system.
Figure 3B:
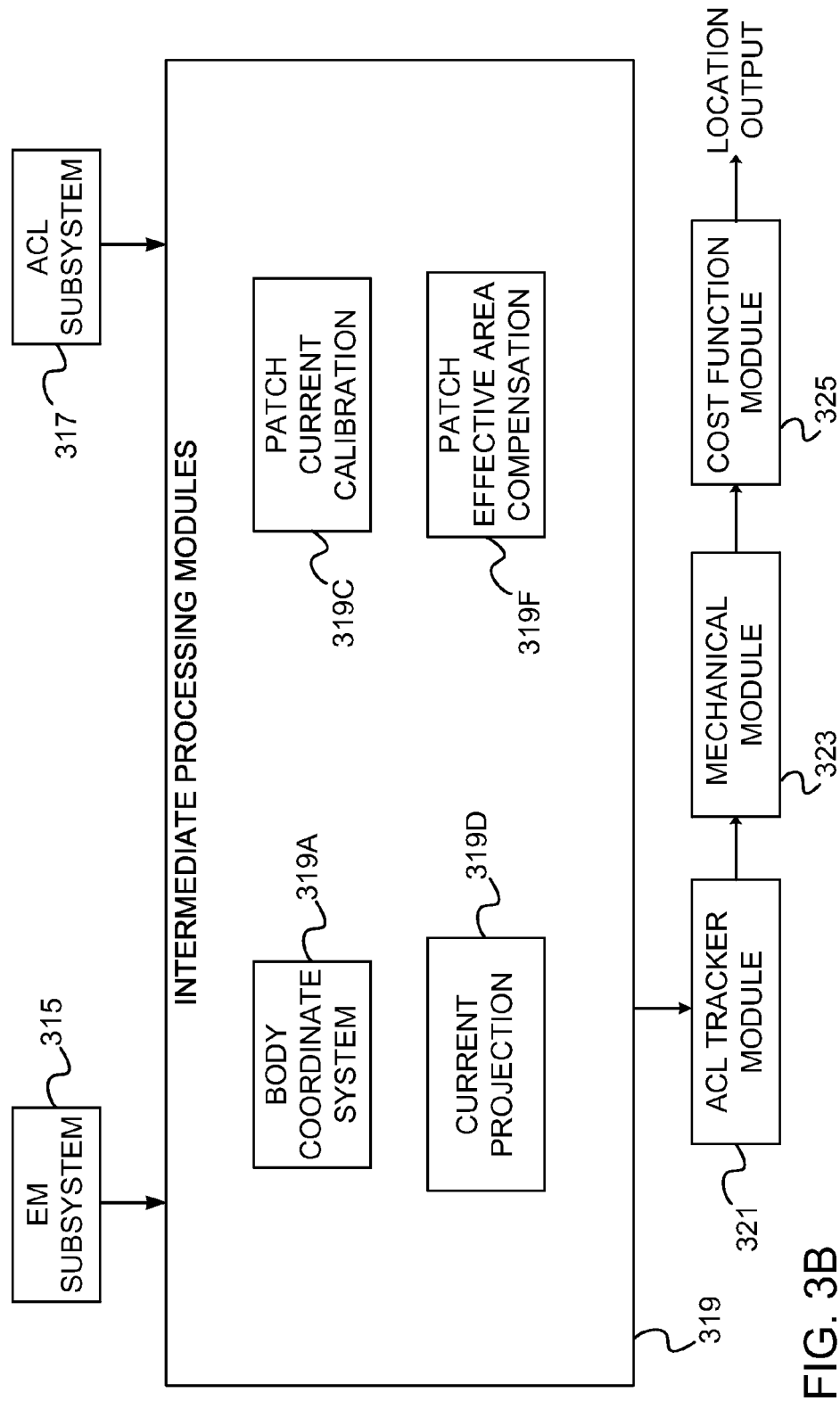
FIG. 3B is a simplified block diagram of the system, according to an embodiment of the present invention.

FIG. 3A is a flow chart 200 schematically illustrating a process for operating system 36, and FIG. 3B is a simplified block diagram of the system, according to an embodiment of the present invention. To implement the process of flow chart 200, professional 56, or another operator of the system, first operates the system in a calibration phase 201, after which the system is operated in a tracking phase 203. Actions performed in each of the steps of the two phases are described in detail below. As is also described below, some of the actions may be performed in either phase. The calibration phase, performed using hybrid catheter 20, comprises steps 204 and 206 of the flow chart. The tracking phase, performed using non-hybrid catheter 21, comprises the remaining steps of the flow chart.

In a reference frame correlation step 204, coordinates measured in an EM reference frame and in an active current location (ACL) reference frame are correlated. An EM tracker sub-system 315 generates measurements in the EM reference frame; an ACL tracker sub-system 317 generates measurements in the ACL frame, also herein termed the Body Coordinate System. The EM tracker sub-system measures locations using the electromagnetic fields generated by coils 24, 26, and 28. The ACL tracker measures locations using currents through ACL patches 60P.

Except where otherwise indicated, the following steps of the flowchart are performed in intermediate processing modules 319, which comprise body coordinate system module 319A, patch current calibration module 319C, current projection module 319D, and patch effective area compensation module 319F.

In an ACL patch calibration step 206, processor 46, using similar currents to those used for step 204, determines differences in individual ACL patch impedances. The differences in the impedances affect the currents in the ACL patches that are measured by the processor. Step 206 concludes calibration phase 201.

In a patch compensation step 208, comprising the first step of tracking phase 203, processor 46 compensates for changes in the ACL patches effective area. The changes are typically caused by factors such as change of conductivity of the patch, usually because of sweating, and partial peeling of the patch from the skin of the patient. Processor 46 uses currents similar to those generated in step 206 to determine compensation factors.

In a current projection step 210, the processor measures the currents in the ACL patches that are generated by currents injected into catheters being tracked, and applies the adjustments determined in steps 206 and 208 to the currents. In step 210 the processor typically also applies adjustments to compensate for temporal components of the currents, for example, drift, heartbeat, and respiration components.

An ACL step 214 comprises an initial training phase, wherein the processor stores current data and location data from the above steps and generates matrices relating the current and location data. ACL step 214 is performed in an ACL tracker module 321. The processor then generates matrices for different "clusters," or regions, of the heart. Once sufficient data has been obtained so that the clusters are sufficiently dense, in a continuation of the ACL step processor 46 applies the generated matrices to the current data from step 210, to calculate preliminary coordinates of apparent locations for electrodes on catheter 21. The preliminary coordinates correspond to the "raw" measured locations of points $M_0, M_1, M_2, M_3$. In preparation for a later, second cost function step of flow chart 200, the preliminary coordinates are parameterized using an adjustment parameter $P_A$, whose function is to improve the accuracy of the measured locations.

In a probe model step 216, performed using a mechanical module 323, processor 46 loads parameters of a model describing the physical properties of catheter 21. The parameters of the model define a free-state shape of the catheter, i.e., the shape of the catheter when no forces are acting on it. Typically the model assumes that the catheter is comprised of a number of linear sections which are connected together at their ends. In addition, the model includes parameters defining a resistance to bending, and a resistance to twisting, of each joint of the connected linear sections.

In a first cost function step 218 performed in a cost function module 325, the processor formulates a first cost function formed of three terms. Each term is a function of the measured locations of the electrodes, and of the calculated locations of the electrodes derived from the model. A first term measures an intrinsic energy of the catheter, a second term measures a position error of elements of the catheter, and a third term measures an orientation error of the elements. The first cost function is minimized to determine a best match between the probe model and the measured locations. The minimized first cost function provides coordinates of model-adjusted locations of the electrodes.

In a second cost function step 219 performed in module 325, the processor formulates a second cost function formed of the differences between the coordinates of the model-adjusted locations and the parameterized coordinates of the preliminary locations.

In a minimization step 220, the processor minimizes the second cost function to determine an optimal value of parameter $P_A$. The minimization is typically performed on an iterative basis, for a given set of measurements for the catheter in one position. In addition, the value of $P_A$ may be determined by using sets of measurements from the catheter in previous positions, typically by applying an adaptive function to the given set and the previous sets. In some embodiments, weights, as described below, may be applied to the sets of measurements.

In a final step 222, the processor applies the optimal value of $P_A$ determined in step 220 to the preliminary coordinates of step 214, in order to formulate improved measured locations of the electrodes of the catheter.

The following description explains each of the steps of flowchart 100 in detail.

Body Coordinate System

Figure 4:
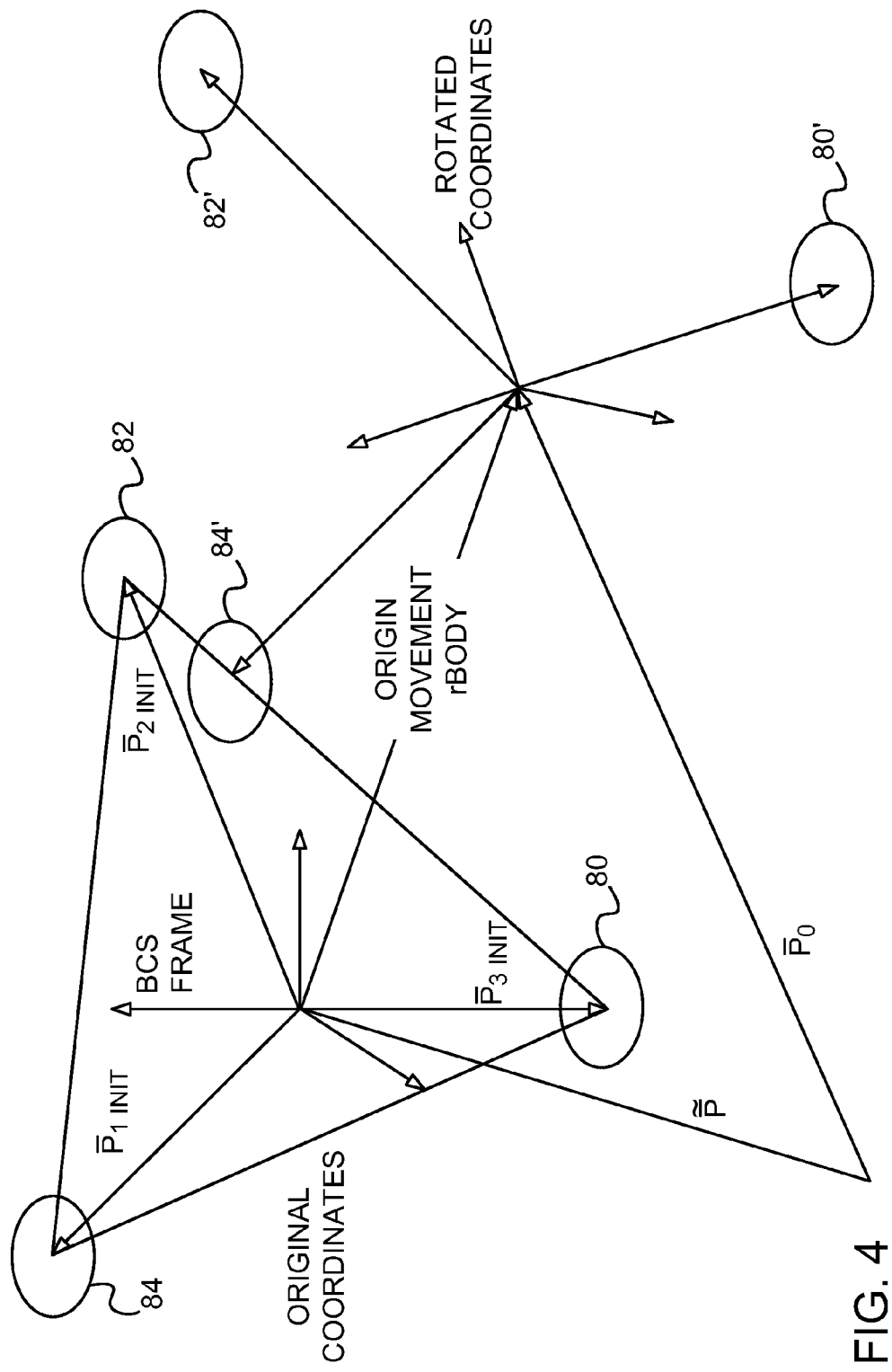
FIG. 4 is a schematic diagram illustrating a vector relationship for reference patches, according to an embodiment of the present invention.

FIG. 4 is a schematic diagram illustrating a vector relationship for reference patches 80R, according to an embodiment of the present invention. Initial positions of the patches are shown as patches 80, 82, and 84. Positions after movement are shown as patches 80', 82', and 84'.

In body coordinate system module 219A, processor 46 applies the relationship in performing reference frame correlation step 204 of flowchart 200. As stated above, system 36 comprises two tracking sub-systems: EM tracker sub-system 315 using sensors such as sensor 22, and ACL tracker sub-system 317 using currents through patches 60P. Each sub-system operates in a respective frame of reference. The EM tracker sub-system operates in an EM frame of reference that is generally fixed with respect to pad 43. The ACL tracker sub-system operates in an ACL frame of reference, the body coordinate system (BCS), that is assumed to be generally fixed with respect to patches 80R. Patches 80R enable measurements made in one of the sub-systems to be converted to the other sub-system. During the calibration phase reference patches 80R are attached to the back of subject 40, so that any motion of the subject with respect to pad 43 is reflected in signal changes in the EM sensors of the reference patches.

In the calibration phase processor 46 analyzes signals from the EM sensors on reference patches 80R, to determine an initial frame of reference for the BCS. During the tracking phase the processor analyzes signals from the EM sensors periodically, to determine changes in the location and orientation of the BCS frame of reference. The processor is able to detect if system parameters have changed beyond those expected, and in this event may return to the calibration phase.

In the calibration phase, the processor accumulates the location of patches 80R in LP coordinates, i.e., coordinates measured relative to location pad (LP) 43, for a time patchInitTime, typically approximately 1 sec.

The processor then calculates the mean location and the standard deviation for each patch:

$$\vec{P1} = \frac{1}{N} \sum_{i}^{N} \vec{P1}_i \quad (1)$$

$$\vec{P1}_{STD} = \sqrt{\sum_{i}^{N} \frac{1}{N} (\vec{P1}_i - \vec{P1})^2},$$

where i is a sample index,
N is the number of samples in time patchInitTime
$\vec{P1}_i$ is a sample value,
$\vec{P1}$ is the mean value of $\vec{P1}_i$ for each patch 1, and
$\vec{P1}_{STD}$ is the standard deviation of $\vec{P1}$.

Providing the value of each $\vec{P1}_{STD}$ is less than a preset figure, typically approximately 1 mm, the calibration is accepted, in which case the mean $\vec{P}$ of all the means is set as the origin the BCS:

$$\vec{P} = \frac{1}{3} \sum_{1}^{3} \vec{P1} \quad (2)$$

The radius vector from each patch to the origin is also calculated and saved for further use:

$$\vec{P}1init = \vec{P}1 - \vec{P} \quad (3)$$

The mean vector defined by equation (2) and the three vectors defined by equation (3) are illustrated in FIG. 4. In addition to the origin, as defined by equation (2), the three vectors of equation (3) define a triangle in a plane, shown in the figure by broken lines between patches 80, 82, and 84. The initial BCS x, y, and z axes are defined using the triangle.

During the tracking phase of system 36, patches 80R may move, as exemplified by patches 80', 82', and 84', and processor 46 measures the new positions of the patches periodically, typically with a period of the order of one second. Embodiments of the present invention assume that the axes defined in the calibration phase move as an approximately rigid body, and processor 46 determines the translation and rotation of the axes from the new patch 80R positions during the tracking phase. Prior to the determinations, the new patch positions are filtered to reduce noise, the filtering typically comprising a low pass filter of the type:

$$y_i = a y_{i-1} + (1-a) x_i, \quad (4)$$

where $y_i$, $y_{i-1}$ are current and previous position estimates,
$x_i$ is the current position measurement, and a is a factor between 0 and 1.

Typically "a" in equation (4) is selected so that there is an effective time constant of approximately 0.5 s in determining current position estimates $\vec{P}1$. Consequently, since body motion is usually slow, such a time constant does not significantly affect performance of system 36.

The filtered positions $\vec{P}1$ are used to determine a new origin vector of coordinates $\vec{P}_0$, substantially as described above for equation (3).

From the filtered positions $\vec{P}1$ processor 46 also determines a rotation matrix T, by methods which will be apparent to those having ordinary skill in the art, relating a new orientation of the axes with the original axes orientation. The processor then applies equation (5) (below) to transform each catheter electrode location measurement back to the original BCS axes.

$$\vec{p}b = T^T \cdot (\vec{p} - \vec{P}_O) \tag{5}$$

where $T^T$ is the transpose of T, $\vec{p}$ is a vector representing a measured catheter electrode location, and $\vec{p}b$ is a vector of the catheter electrode relative to the original BCS axes.

The vector $\vec{p}$ is calculated in ACL step 214, described below.

Patch Current Calibration

Ideally the impedance of each ACL patch measured to ground is zero, but this may not be the case in practice. If the impedances are different from zero, the measured currents through the patches may lead to errors in the predicted location of a catheter such as catheter 20, so that to reduce such errors, processor 46 uses a patch current calibration module 219C to perform a calibration on the ACL patches in patch calibration step 206 (FIGS. 3A and 3B). The calibration compensates for the impedances being non-zero, and also for differences in the impedances between the patches. The calibration enables processor 46 to estimate the current that would flow in a patch if the patch impedance is zero.

Figure 5:
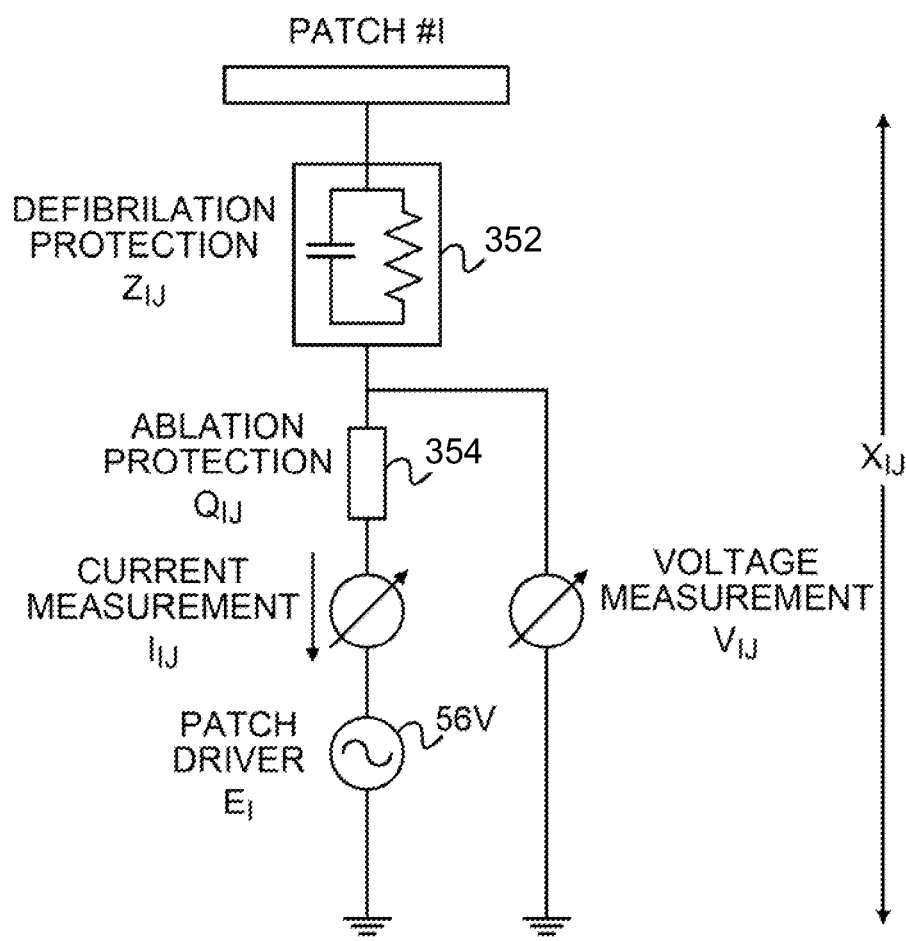
FIG. 5 is a schematic illustration of a patch circuit, according to an embodiment of the present invention.

Reference is now made to FIG. 5, which is a schematic illustration of an ACL patch circuit, according to an embodiment of the present invention.

All ACL patches have generally similar circuits. Each ACL patch i comprises a defibrillation protection circuit 352 and an ablation protection circuit 354. The two circuits are connected in series between the patch and ground. In FIG. 5, and for the analysis below, for each patch i, j is a frequency index, denoting the frequency $f_j$ transmitted by the patch.

$z_{ij}$ is a known impedance of defibrillation protection circuit 352. The known impedance may typically be provided by a patch box manufacturer, or determined from analysis of circuit 352.

$q_{ij}$ is the impedance of ablation protection circuit 354. The ablation protection circuit impedance is estimated during a patch impedance calibration process, described below.

$E_j$ is a voltage, from a voltage source 56V, that drives patch i with frequency $f_j$.

$I_{ij}$ is a current measured through patch i at frequency $f_j$.

$V_{ij}$ is a voltage measured on patch i at frequency $f_j$.

$X_{ij}$ is the actual voltage on patch i at frequency $f_j$.

In a patch impedance calibration procedure for system 36, processor 46 uses a respective voltage source 56V to inject current into each patch i at a corresponding frequencies $f_j$. The injected currents are also used in a patch effective area compensation procedure, described below.

The currents are injected at different frequencies j, and control unit 44 comprises ADCs (analog-to-digital circuits) which processor 46 multiplexes to measure values of $V_{ij}$ sequentially and values of $I_{ij}$ simultaneously.

In the patch impedance calibration procedure the processor estimates a value of $q_{ij}$ from the values of $V_{ij}$ and $I_{ij}$, typically by finding the ratio $$\frac{V_i}{I_i}$$

at each frequency j, and finding a best fit, typically a best quadratic fit, across the measured frequencies. Thus:

$$q_{ij} = \hat{q}_i(f_j) = \left[\frac{\hat{V}_{ij}}{\hat{I}_{ij}}\right] \tag{6}$$

During the tracking phase, processor 46 measures the values of $I_{ij}$ and $\Sigma_i V_{ij}$ at the different operating frequencies f. In the following analysis, the expressions of equation (7) are assumed.

$$\tilde{V}_j \equiv \sum_i V_{ij}, \text{ and } E_{ij} \equiv \delta_{ij} E_j \tag{7}$$

where $\tilde{V}_j$ is the sum of voltages measured on all patches at a frequency $f_j$, and $\delta_{ij}$ the Kronecker delta.

For a particular patch i being driven at a frequency j, applying Ohm's law to ablation protection circuit 354 gives:

$$V_{ij} = E_{ij} + q_{ij} I_{ij},$$

so that $$\tilde{V}_j \equiv \sum_i V_{ij} = \sum_i (E_{ij} + q_{ij} I_{ij}) = \sum_i (\delta_{ij} E_j + q_{ij} I_{ij}) = E_j + \sum_i q_{ij} I_{ij}$$

which rearranged gives:

$$E_j = \tilde{V}_j - \sum_i q_{ij} I_{ij} \tag{8}$$

Applying Ohm's law and equation (8) to the complete circuit of FIG. 5 gives, for a particular patch i:

$$X_{ij} = E_{ij} + (q_{ij} + z_{ij}) I_{ij} \tag{9}$$

$$= \delta_{ij} E_j + (q_{ij} + z_{ij}) I_{ij}$$

$$= \delta_{ij} \left(\tilde{V}_j - \sum_k q_{kj} I_{kj}\right) + (q_{ij} + z_{ij}) I_{ij}$$

where $X_{ij}$ is the overall voltage on patch i at frequency j.

The values of equation (9) may be used to determine a body conductance matrix $\sigma$, where $\sigma$ is defined by the matrix equations:

$$-I = \sigma \cdot X, \text{ or a } \sigma = -I \cdot X^{-1} \tag{10}$$

where I is a matrix of patch currents, and X is a matrix of patch voltages. The patch currents may also be written as a vector s. The negative sign in equation (10) assumes a convention that positive current flows into body 40, and positive currents are also measured flowing out of the body. Alternatively, an equation similar to equation (10), using an impedance matrix Im, may be written relating matrices I and X.

Those having ordinary skill in the art will understand that a system conductance matrix σ', which is a combination of the body conductance matrix σ and a patch resistance matrix $R_k$, is given by:

$$\sigma' = (Id + \sigma \cdot R_k)^{-1} \cdot \sigma \quad (11a)$$

where Id is the identity matrix
σ is the conductance matrix defined in equation (12), and
$R_k$ is a diagonal matrix of patch resistances, with $(z_{ik}+q_{ik})$ as the $i^{th}$ diagonal element, for a catheter transmitting a frequency $f_k$.

If a voltage V is applied to the system, the current flowing in the system is given by:

$$\tilde{s} = \sigma' \cdot V = (Id + \sigma \cdot R_k)^{-1} \cdot \sigma \cdot V \quad (11b)$$

where V is a voltage vector, and
$\tilde{s}$ is the measured current vector at frequency $f_k$.

Equation (11b) shows that $\tilde{s}$ is affected by the patch resistances. A calibrated current, that does not depend on the patch resistances and thus does not depend on frequency $f_k$, may be defined as:

$$s \equiv \sigma \cdot V = (Id + \sigma \cdot R_k) \cdot \tilde{s} \quad (11c)$$

where s is a calibrated current vector.

Processor 46 passes the estimated current values in each patch given by vector s to a patch effective area compensation process, described below.

Patch Effective Area Compensation

The description in this section explains patch compensation step 208 (FIG. 2A), wherein in patch effective area module 319F processor 46 performs a process that compensates for changes in the effective area of ACL patches i. In this section, patches 60P are differentiated by being referred to as patch i and patch j. Some causes of changes to the effective area of the ACL patches are partial peeling of a patch from patient body 40, and skin conductivity changes, typically due to sweating. A patch effective area compensation model assumes that $$R_{ij} = G \cdot C_i \cdot C_j \cdot d_{ij} \quad (12)$$

where $R_{ij}$ is the impedance between patch i and patch j.
$C_i$, $C_j$ are effective areas of patch i and patch j
$d_{ij}$ is the distance between patches i and j, and
G is a constant of proportionality which is a function of, inter alia, medium conductivity.

In implementing the area compensation process, processor 46 generates a current $I_j$ from source patch j, and measures each of the currents $I_{ij}$ received in the other patches. Processor 46 performs the process for each ACL patch, so that for N patches, the processor makes a total of N(N−1) current measurements.

An estimated impedance $m_{ij}$ between any two patches j, is given by:

$$m_{ij} = \frac{V_j}{I_{ij}} \quad (13)$$

where $V_j$ is the voltage driving patch j.
From equation (13) a normalized estimated impedance $\hat{m}_{ij}$ is given by:

$$\hat{m}_{ij} = \frac{m_{ij}}{\sum_{\substack{k=1,\\k\neq j}}^{k=N} m_{kj}} = \frac{V_j/I_{ij}}{\sum_{\substack{k=1,\\k\neq j}}^{k=N} V_j/I_{kj}} = \frac{1/I_{ij}}{\sum_{\substack{k=1,\\k\neq j}}^{k=N} 1/I_{kj}} \quad (14)$$

Processor 46 calculates and stores the values of $\hat{m}_{ij}$, using equation (14), during implementation of the area compensation process.

The current $I_j$ generated at patch j divides between the other patches in inverse proportion to the impedance between patch j and the other patches. Thus, the current $I_{ij}$ from source patch j to receiving patch i is given by:

$$I_{ij} = I_j \frac{1/R_{ij}}{\sum_{k,k\neq j} 1/R_{kj}} \quad (15)$$

Substituting equation (11) into equation (15) gives:

$$I_{ij} = \frac{I_j}{GC_iC_jd_{ij}\sum_{k,k\neq j} 1/(GC_kC_jd_{kj})} = \frac{I_j}{C_id_{ij}\sum_{k,k\neq j} 1/(C_kd_{kj})} \quad (16)$$

Substituting the value for $I_{ij}$ into equation (14), and simplifying, gives:

$$\hat{m}_{ij} = \frac{C_id_{ij}}{\sum_{n,n\neq j} C_nd_{nj}} \quad (17)$$

where n is an integer from 1 to N, and N is the number of ACL patches.

Equation (17) may be written:

$$\sum_{n,n\neq j} (\hat{m}_{ij} - \delta_{ij})C_nd_{nj} = 0 \quad (18)$$

As described above, processor 46 has determined the values of the relative impedances $\hat{m}_{ij}$.

In equation (18), inter-patch distances $d_{ij}$ may be measured using their respective associated tracking coils (and, when i=j, $d_{ij}$=0).

Equation (18) is a system of N(N−1) equations with N unknowns, i.e., the values $C_1, C_2, \ldots, C_N$. The system of equations (18) may be used to find the relative values of $C_i$. The system of equations is of the type $A \cdot \vec{C} = 0$ wherein A is an N(N−1)×N matrix that depends on $\hat{m}_{ij}$ and $d_{ij}$, and wherein $\vec{C}$ is a vector representing the N values of Singular value decomposition (SVD) analysis of A or eigenvector analysis of the N×N matrix $A^TA$ provides a solution for $\vec{C}$, as is known in the art.

Assuming that processor 46 performs eigenvector analysis of the matrix $A^TA$, the processor selects the eigenvector with the smallest eigenvalue. Typically, the values of $\hat{m}_{ij}$ and $d_{ij}$ for matrices A and $A^T$ are filtered with a filter similar to equation (4), where the filter is adjusted to have a time constant of the order of 10 seconds. The smallest eigenvector corresponds to normalized values of the 6 areas $C_i$, herein termed $Ea_i$. Typically, processor 46 calculates the values of $Ea_i$ periodically, with a period that may be set by operator 56. In one embodiment, the period is of the order of 1 second.

The estimated current vector s, derived from equation (11c), gives 6 respective values of the currents $I_i$ in the ACL patches. To compensate for the patches effective area, $Ea_i$, processor 46 forms a normalized value of each of the currents:

$$In_i = \frac{I_i \cdot Ea_i}{\sum_{i=1}^{i=6} I_i \cdot Ea_i} \equiv (In6) \quad (19)$$

where (In6) is a six-dimensional current vector.

The normalization removes effects caused by changes in effective resistance in the region of the catheter electrode, such as may be caused by the electrode coming into contact with tissue, inhomogeneity of material surrounding the electrode, and/or instability of the source injecting current into the catheter electrode.

Current Projection

The 6 currents given by equation (19) have only five degrees of freedom since their sum is always one. To prevent singularities in further analysis of the currents, in current projection step 210 the 6 currents are converted, using a projection matrix J, to five independent quantities in current projection module 119D. Projection matrix J is derived by orthogonalization of a matrix, $$\begin{pmatrix} 1 & 1 & 1 & 1 & 1 & 1 \\ 0 & 1 & 0 & 0 & 0 & 0 \\ 0 & 0 & 1 & 0 & 0 & 0 \\ 0 & 0 & 0 & 1 & 0 & 0 \\ 0 & 0 & 0 & 0 & 1 & 0 \\ 0 & 0 & 0 & 0 & 0 & 1 \end{pmatrix},$$

taking only the last five row vectors of the resulting matrix.

After orthogonalization, the last five rows of the orthogonalized matrix give:

$$J = \begin{pmatrix} -\frac{1}{\sqrt{30}} & \sqrt{\frac{5}{6}} & -\frac{1}{\sqrt{30}} & -\frac{1}{\sqrt{30}} & -\frac{1}{\sqrt{30}} & -\frac{1}{\sqrt{30}} \\ -\frac{1}{2\sqrt{5}} & 0 & \frac{2}{\sqrt{5}} & -\frac{1}{2\sqrt{5}} & -\frac{1}{2\sqrt{5}} & -\frac{1}{2\sqrt{5}} \\ -\frac{1}{2\sqrt{3}} & 0 & 0 & \frac{\sqrt{3}}{2} & -\frac{1}{2\sqrt{3}} & -\frac{1}{2\sqrt{3}} \\ -\frac{1}{\sqrt{6}} & 0 & 0 & 0 & \sqrt{\frac{2}{3}} & -\frac{1}{\sqrt{6}} \\ -\frac{1}{\sqrt{2}} & 0 & 0 & 0 & 0 & \frac{1}{\sqrt{2}} \end{pmatrix} \quad (20)$$

The currents from equation (19) are thus projected to five current-equivalents according to equation (23):

$$(In5) = J \cdot (In6) \quad (21)$$

In addition to performing the normalization of equation (21) in current projection step 210, processor 46 may also allow for temporal components, such as those caused by drift, heartbeat, and respiration, in the normalized current signals. A method for compensating for temporal components is given in US Application 2010/0079158 which is assigned to the assignees of the present invention, and which is incorporated herein by reference. For simplicity, the following description does not include allowance for temporal components, and those having ordinary skill in the art will be able to adapt the description, mutatis mutandis, to allow for such components.

ACL Tracker

In ACL step 214 ACL tracker module 321 calculates the location of catheters such as catheter 20 and the electrodes of catheters such as catheter 21, using the current measurements generated in step 210. The measurements generated in step 210 are combined into a current-to-position mapping (CPM) vector $\vec{m}$.

Figure 6:
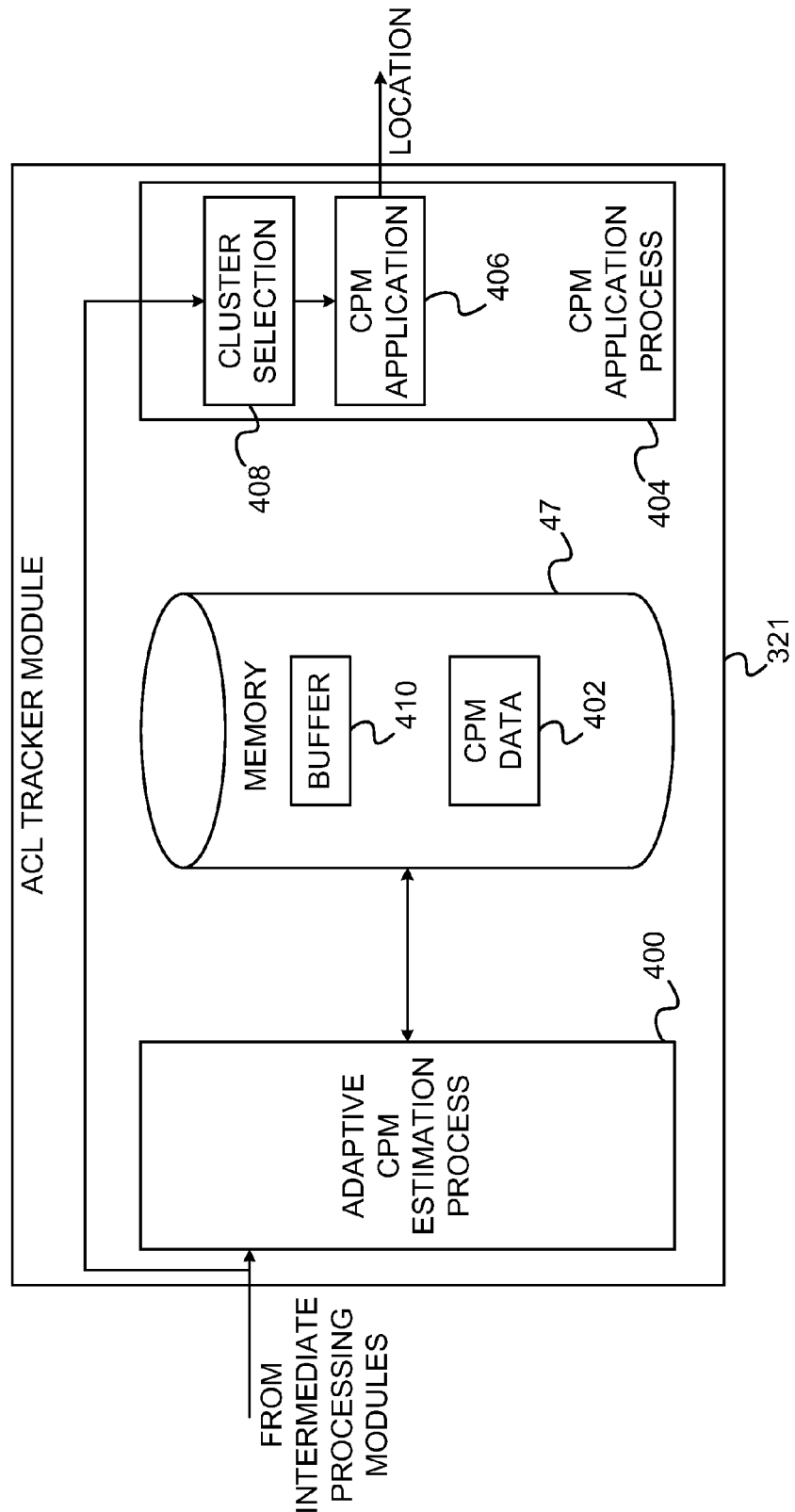
FIG. 6 is a simplified block diagram illustrating components of a tracker module, according to an embodiment of the present invention.
Figure 7:
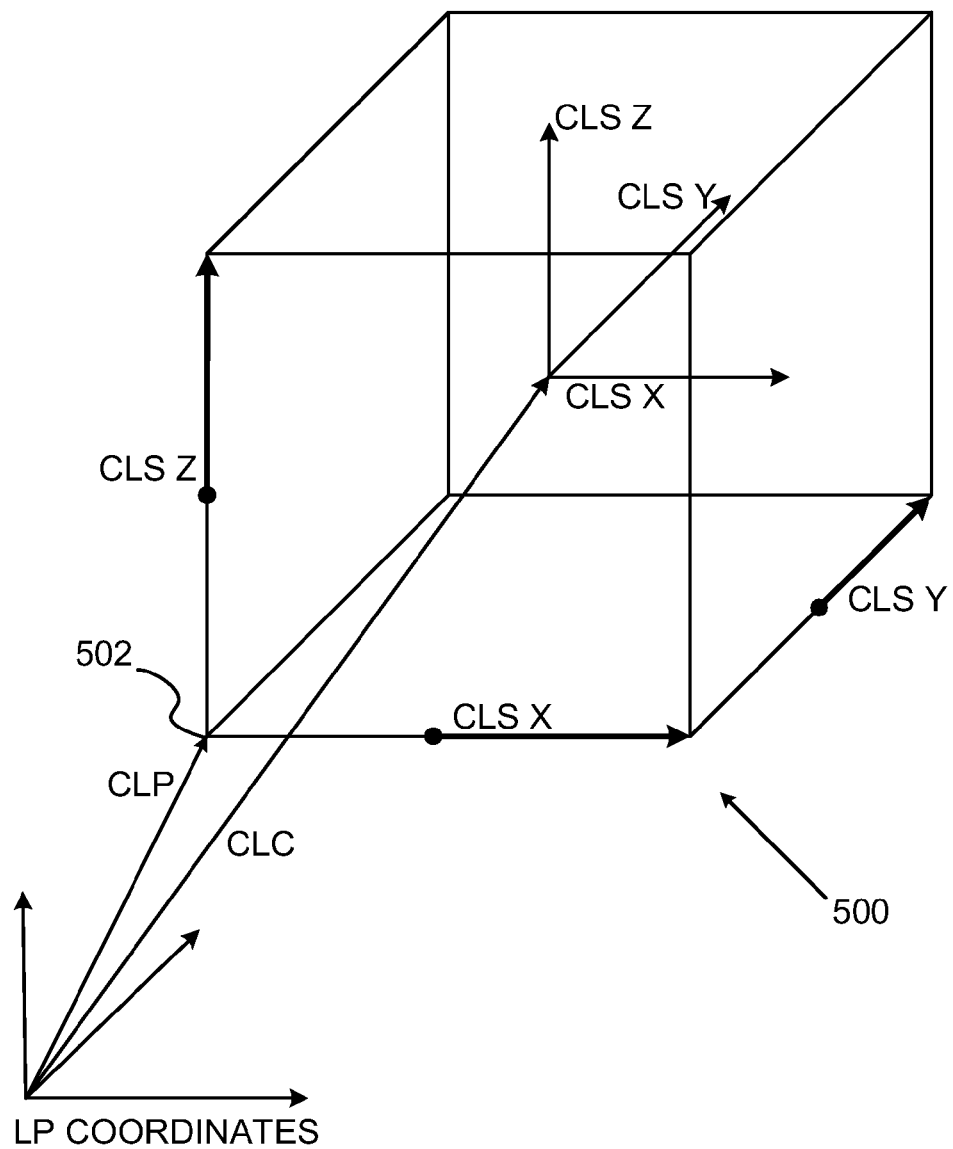
FIG. 7 is a diagram showing parameters used in defining sub-volumes into which a region being investigated is divided, according to an embodiment of the present invention.

FIG. 6 is a simplified block diagram illustrating components of the ACL tracker module, and FIG. 7 is a diagram showing parameters used in defining sub-volumes into which the region being investigated is divided, according to embodiments of the present invention.

The ACL tracker module comprises two components, an adaptive CPM estimation process 400 and a CPM application process 404. CPM application process 404 further comprises a cluster selection module 408, and a CPM application module 406, the functions of which are described below.

The adaptive CPM estimation process uses measurements from any hybrid catheter having an EM sensor and associated electrode, such as catheter 20, the measurements being included in vectors $\vec{m}$, to calculate CPM matrices. In embodiments of the present invention, a respective matrix is calculated for each sub-volume 500, also herein termed a cluster volume or a cluster, of the region being investigated. The region being investigated is divided into different sizes of clusters according to a resolution set for a particular cluster level. Thus, at a low resolution level the region may be divided into 16 clusters, each cluster having a matrix. At a higher resolution, the region may be divided into 1024 clusters having respective matrices.

The matrices constructed in the CPM estimation process take time to build, so that there is an initialization period for ACL step 214 during which period processor 46 receives initial data from current projection step 210. For a particular cluster, once the processor has accumulated sufficient data for that cluster, the processor is able to generate a matrix for the cluster. The generated matrix is stored as CPM data 402 in memory 47 of control unit 44 (FIG. 1A).

The CPM application uses the generated matrices, with current measurements for each cathode electrode, to calculate each electrode location in real-time. The calculation is performed according to the following equation:

$$\vec{p} = A \cdot \vec{m} \quad (22)$$

where $\vec{m}$ is the CPM vector built from the current measurements,

A is the matrix for a particular cluster, and $\vec{p}$ is the position vector of the electrode, also referred to in equation (5) above.

The CPM vector $\vec{m}$ typically comprises 5 current elements, corresponding to the values derived from equation (21), and may comprise other elements, for example temporal correction elements. For simplicity, the following description refers only to the 5 current elements, and those having ordinary skill in the art will be able to adapt the description, mutatis mutandis, to account for other elements.

FIG. 7 illustrates parameters used to define cluster sub-volume 500. The parameters used are vectors measured in the EM tracker frame of reference (FIG. 4) Each cluster sub-volume 500 is referenced by its left-rear-bottom corner 502, also herein termed the cluster origin, which is a vector $\vec{Clp}_{RL}$ having the lowest values of x, y, and z for any point comprised in the cluster. Cluster sub-volume 500 is defined by its center, Clc, rectilinear lengths Cls from the center, and a cluster resolution level vector $Clr_{RL}$, which defines lengths of the sides of clusters at a resolution level RL.

Measured in mms, typical default values of Clc and Cls and $Clr_{RL}$ are:

Clc=(0, 0, 280)
Cls=(150, 150, 200)
$Clr_{RL}$=(50, 20, 5), for a resolution level RL=1 (the coarsest resolution). For larger values of RL, corresponding to higher resolutions, the values of the coordinates of $Clr_{RL}$ decrease.

The default values of Cls and $Clr_{RL}$ correspond to a volume that is a box having dimensions of 300 mm×300 mm×400 mm. This volume is divided into equal-sized clusters having smaller dimensions. For the default values given above there are 6×15×80 clusters in the box.

For a given location $p_i$, a cluster index of an associated cluster is found by calculating the following expressions:

$$Cldim = 2\frac{Cls}{Clr_{RL}} + (1, 1, 1) \quad (23)$$

$$ClRng = (Cldim_y Cldim_Z, Cldim_Z, 1)$$

$$Clx_{i,RL} = \left\lfloor \frac{\overline{p_i} - Clc + Cls}{Clr_{RL}} \right\rfloor \cdot ClRng + 1$$

In expressions (23):

Cldim is a vector (Cldim$_x$,Cldim$_y$, Cldim$_z$), where the coordinates of the vector correspond to the number of clusters in each dimension;

Vector division is evaluated by dividing each element of the vector numerator by the corresponding element of the vector denominator, so that, for example, $$\frac{(20, 30, 40)}{(5, 6, 4)} = (4, 5, 10);$$

The vector multiplication in the last expression is a dot, or scalar, product.

Given a cluster index $Clx_{i,RL}$, the cluster origin is found by applying the following expressions recursively:

$$Clx_{i,RL} = Clx_{i,RL} - 1 \quad (24)$$

$$\left( q_j = \left\lfloor \frac{Clx_{i,RL}}{ClRng_j} \right\rfloor, (Clinx = Clinx - q_j ClRng_j) \right), \{j = 1, 2, 3\}$$

$$\vec{Clp}_{RL} = qClr_{RL} + Clc - Cls$$

where Clinx has an initial value $Clx_{i,RL}$.

The update holder referred to above is an index that flags locations that have been used to update the cluster CPM matrix. The index prevents multiple measurements from a location being used to calculate the matrix. An update holder index (Uhl) is calculated as follows:

$$Uhl = \lfloor \{ClNo(\vec{p} - \vec{Clp}_1)/Clr_1 + ClNo\}\rfloor \cdot \{(3ClNo)^3, (3ClNo)^2, ClNo\} + 1 \quad (25)$$

Figure 8:
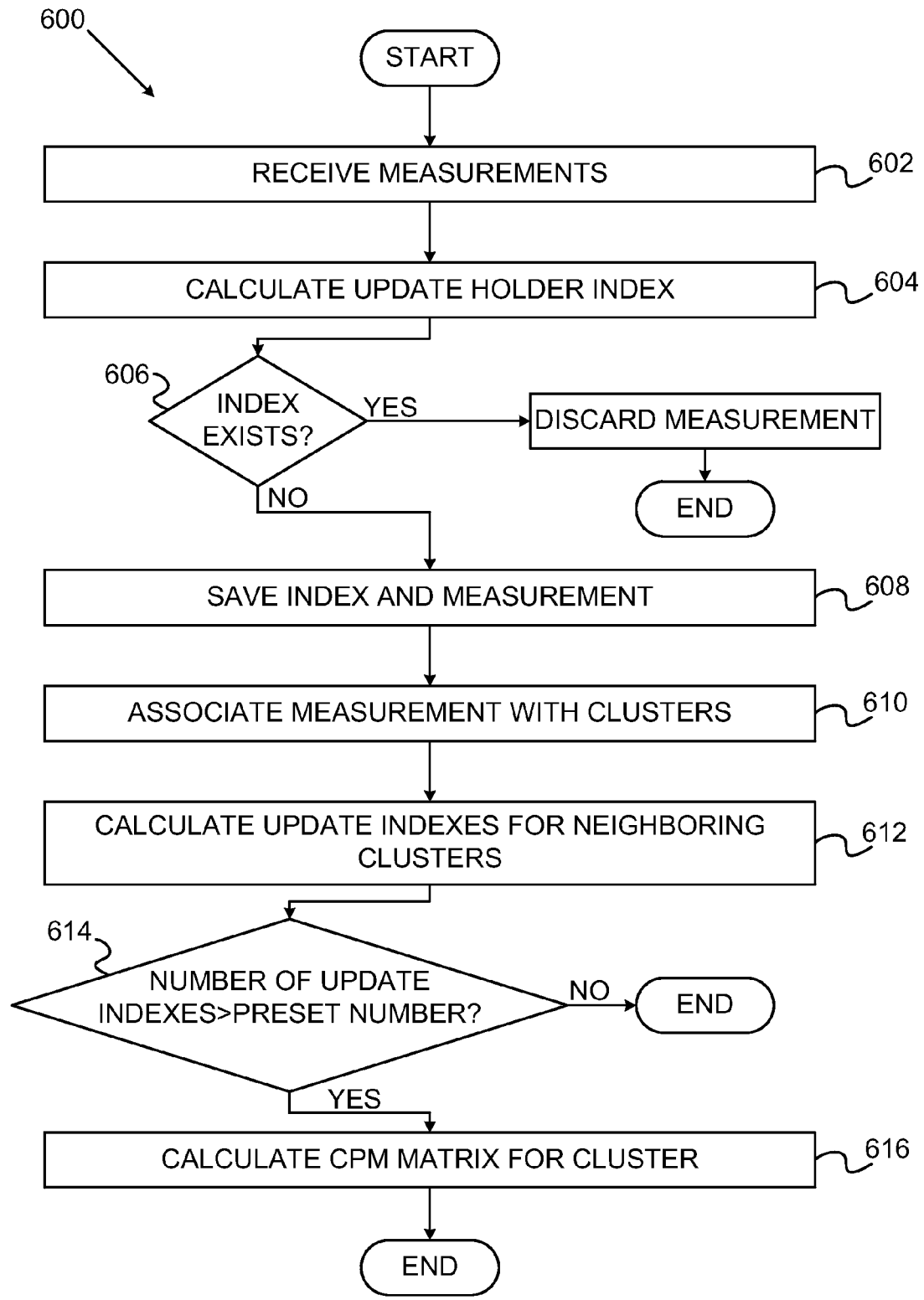
FIG. 8 is a flowchart showing steps to generate current to position matrices, according to an embodiment of the present invention.

FIG. 8 is a flowchart 600 showing steps taken by processor 46 to generate CPM matrices, according to an embodiment of the present invention. The steps of the flowchart are performed in adaptive CPM estimation process 400 (FIG. 6) as each measurement is generated by hybrid catheter 20.

In an initial step 602, measurements are received from any hybrid catheter, and the processor forms the measurements into a CPM vector $\vec{m}$, as described above.

In a first update holder step 604, the update holder index for the measurement is calculated, using equation (25).

In a first condition 606, the processor checks to see if the update holder index already exists, by checking to see if the index has been saved in memory 47.

If the index does exist, the measurement is discarded and the flowchart ends.

If the index does not exist, then in a save step 608 the index and the measurements are saved in a buffer 410 (FIG. 6) in memory 47. The measurements are saved as a vector $\vec{m}$.

In a cluster association step 610, the measurement is associated with corresponding clusters. The association is performed by calculating from the measurement the corresponding cluster index, according to equation (23). The measurement is associated with this cluster index.

The cluster origin, $\vec{Clp}_{RL}$, is then calculated, using equation (24). From this point, the cluster origins of all existing nearest neighbor clusters, up to 26 of which are possible in total, are found using equation (26):

$$\vec{Clp}_{RL,n} = \vec{Clp}_{RL} + d_n Clr_{RL}, n = 1 \ldots 26, \quad (26)$$

where $d_n = \{\{-1, -1, -1\}, \{-1, -1, 0\}, \{-1, -1, 1\}, \{-1, 0, -1\},$ $\{-1, 0, 0\}, \{-1, 0, 1\}, \{-1, 1, -1\}, \{-1, 1, 0\}, \{-1, 1, 1\},$ $\{0, -1, -1\}, \{0, -1, 0\}, \{0, -1, 1\}, \{0, 0, -1\},$ $\{0, 0, 1\}, \{0, 1, -1\}, \{0, 1, 0\}, \{0, 1, 1\}, \{1, -1, -1\},$ $\{1, -1, 0\}, \{1, -1, 1\}, \{1, 0, -1\}, \{1, 0, 0\}, \{1, 0, 1\},$ $\{1, 1, -1\}, \{1, 1, 0\}, \{1, 1, 1\}\}$ From the values of $\vec{Clp}_{RL}$ the cluster indexes of all the nearest neighbor clusters are calculated from equation (23). The calculations in this step are applied for all values of RL.

In a second update holder step 612, the update holder indexes for the neighboring clusters are calculated using the measurement received in step 602 and equation (25). If an update index is not already occupied, the measurement is placed in a buffer 310 (FIG. 6), and the index is saved. If the index is already occupied, no action is taken.

In a second condition 614, the number M of update indexes in each cluster Clx is evaluated. If M is larger than a preset number, typically of the order of 40, then in a cluster matrix step 616 the CPM matrix A of the cluster is calculated, using equation (27):

$$A_{Clx,RL} = [\vec{m}_1; \vec{m}_2; \ldots \vec{m}_M]^{-1} \cdot [\vec{p}_1; \vec{p}_2; \ldots \vec{p}_M] \quad (27)$$

where $\vec{p}_n$ is the measured location of the hybrid catheter, and $\vec{m}_n$ is the CPM vector, described above with reference to equation (22), for update index n, n=1, 2, . . . M.

Typically, in the case of a reference catheter such as CSRC 27 being used, two CPM matrices A are calculated for each cluster, one using measurements with the reference catheter, one without the reference catheter measurements, and flowchart 600 then ends.

If in condition 614 M is not larger than the preset number, flowchart 600 ends.

Typically, the calculations in flowchart 600 are checked at various stages, to verify that the calculated results are self-consistent. For example, in cluster association step 610, if the number of existing neighboring clusters is less than a preset number, for example 4, an error may be assumed and the measurement of step 602 is not accepted. Other self-consistency checks for the operation of the flowchart will be apparent to those having ordinary skill in the art.

FIG. 9 is a flowchart 700 showing steps taken by processor 46 to generate catheter positions using the CPM matrices generated in flowchart 600, according to an embodiment of the present invention. The flowchart uses the measurements that are also used to generate the CPM matrices.

An initial step 702 is generally similar to initial step 602 (FIG. 8), wherein measurements are received from a hybrid catheter, and the processor forms the measurements into a CPM vector $\vec{m}$.

If the measurement $\vec{m}_1$ is the first measurement from the catheter, then in a position calculation step 704, in cluster selection module 408 the lowest cluster resolution, RL=1, is selected. An estimate $\hat{\vec{p}}_1$ of the position is made according to equation (28):

$$\hat{\vec{p}}_1 = \text{Min}(\vec{m}_1 \cdot A_{Clx,1} - \vec{C}lp_1(Clx)); Clx=1 \ldots M \quad (28)$$

where Clx is a cluster index for CPM matrices $A_{Clx,1}$, that is assumed to vary from 1 to M; and $\vec{C}lp_1(Clx)$ is the cluster origin of the cluster with index Clx, calculated according to equation (23).

In a first condition 703 the value from equation (28) is checked to ensure it is within the cluster volume (with cluster index Clx), by verifying that:

$$\|\hat{\vec{p}}_1 - \vec{C}lp_1(Clx)\| < \sqrt{3} Clr_1 \quad (29)$$

Equations (28) and (29) are applied to incoming measurements until expression (29) is valid, producing a first valid position estimation $\hat{\vec{p}}_1$.

For subsequent measurements $\vec{m}_i$, i.e., in subsequent measurement steps 705, the validity of the determined position is checked by evaluating the difference between the immediately preceding position estimates, and verifying that the difference does not exceed a preset value. If the difference is exceeded, the measurement is discarded.

In a resolution level step 706, the cluster indexes for all resolution levels RL are calculated, using equation (23). In addition, the neighboring cluster indexes n are identified, using the process described above with respect to equation (26).

In a multiple location step 708, CPM matrices A that are valid, for the clusters identified in step 706, are used to determine estimated positions for measurement $\vec{m}_i$, according to equation (30):

$$\hat{\vec{p}}_{i,RL,n} = \vec{m}_i \cdot A_{Rl,n} \quad (30)$$

In a location estimation step 710, the values determined in equation (30) are weighted, using a Gaussian weighting factor:

$$w_{RL,n} = \frac{1}{\sqrt{2\pi} \, Clr_{RL}} e^{-\frac{(\vec{C}lp_{RL,n} - \hat{p}_{i-1})^2}{Clr_{RL}^2}} \quad (31)$$

Processor 46 uses the weighting factor to form a final weighted sum of all clusters at all levels, generating a preliminary location for each electrode, according to equation (32):

$$\hat{\vec{fp}}_i = \frac{\sum_{RL,n} w_{RL,n} \cdot \hat{\vec{p}}_{i,RL,n}}{\sum_{RL,n} w_{RL,n}} \quad (32)$$

The preliminary locations from equation (32) are for electrodes 100, 102, 104, and 104 and are based on measured currents between the electrodes and patches 60P. The estimated locations correspond to locations $M_0$, $M_1$, $M_2$, $M_3$ (FIG. 2A). In preparation for cost function step 219 (FIG. 3A), the preliminary locations are converted to parameterized preliminary locations, according to equation (33):

$$\vec{pfp}_i = \vec{fp}_i \cdot P_A \quad (33)$$

where $\vec{pfp}_i$ are the parameterized preliminary locations, and $P_A$ is a parameter matrix. Parameter $P_A$ is applied to the preliminary locations to improve the final locations determined by processor 46. As described below, the processor evaluates an optimal value for $P_A$ and applies the optimal value to determine final locations of the electrodes.

Mechanical Probe Model

Referring back to FIGS. 2A and 2B and the descriptions of the figures, embodiments of the present invention determine the best match between the points $E_0$, $E_1$, $E_2$, $E_3$, and the measurements $M_0$, $M_1$, $M_2$, $M_3$, i.e., the values of $\vec{fp}_i$ determined in equation (32), within the constraints of a probe model. The calculated locations of points $E_0$, $E_1$, $E_2$, $E_3$, are constrained by the model to be on the sections 122, 124 and 126, but the actual position transducers (i.e., electrodes 100, 102, 104 and 106) may not be precisely at these points.

In probe model step 216 of flowchart 200, processor loads parameters of a physical model that define physical properties of probe 21. The physical properties in its free state are defined by the parameters $\{N, L_k, G_k(d), P_k\}$ wherein:

N—Number of sections, and k is an index of a section.

$L_k$—Section lengths (which need not be equal), $0 \leq k < N$.

$G_k(d)$—Rotation matrix as a function of deflection parameters d for deflectable probes (or a constant matrix for pre-shaped probes), $1 \leq k < N$. This matrix represents the relative rotation between section k and section (k−1) when no external forces are applied (i.e., force free shape).

d are values of parameters representing deflection from the force free shape, applicable to a deflectable probe.

$P_k$—List of position transducers, i.e., electrodes, on section k, where $0 \leq k < N$. Each position transducer is represented by its distance from the section start and its relative importance (its weight in calculating a cost function, denoted by $w_j^{model}$, discussed below). The list for each section can contain any number of position transducers, including zero.

The physical properties of probe 21 are described by the parameters $\{A_k, B_k\}$ which respectively represent the resistance of a joint between section k and section (k−1) against bending and twisting.

First Cost Function

This section describes the cost function that is formulated in step 218 of flowchart 200. A state of probe 21, i.e., the positions and orientations of the different section lengths, is given by the set of variables:

$$\{x_0, r_k, d\} \tag{34}$$

where $r_k$ is the orientation of section k relative to section k−1 for 0<k<N and the global orientation of the first section for k=0:

$$r_k \equiv \begin{cases} O_{k-1}^T \cdot O_k & 0 < k < N \\ O_0 & k = 0 \end{cases} \tag{35}$$

The terms $x_0$ (a vector) and $O_k$ (a matrix) are defined above with respect to FIG. 2B.

For adjacent sections of the modeled probe, an orientation difference between the actual relative orientation and the current deflection is:

$$dr_k = r_k^T \cdot G_k(d) \tag{36}$$

The processor converts this orientation difference to the bend and twist angles:

$$\{\alpha_k, \beta_k\} = \text{Angles}(dr_k) \tag{37}$$

The function Angles(r) wherein r is a unitary 3×3 matrix that represents rotation, is defined as follows:

$$\{\alpha, \beta\} \equiv \text{Angles}\left(\begin{bmatrix} r_{11} & r_{12} & r_{13} \\ r_{21} & r_{22} & r_{23} \\ r_{31} & r_{32} & r_{33} \end{bmatrix}\right) \tag{38}$$

$\alpha = \arccos(r_{33})$ $\beta = \arctan(r_{11}(1 + r_{33}) - r_{31}r_{13}, r_{12}(1 + r_{33}) - r_{32}r_{13})$ where:

arctan(x, y) is the angle between the vector(x, y) and the x axis.

The processor calculates an intrinsic energy score, as a first term of the cost function, using the probe model parameters $\{A_k, B_k\}$, according to equation (39):

$$E^{int} = \sum_{k=1}^{N-1} A_k \alpha_k^2 + B_k \beta_k^2 \tag{39}$$

The processor calculates a weighted position error score as a second term of the cost function. The score represents a position difference between the locations of the position transducers, $E_0, E_1, E_2, E_3$, given by the probe model and the actual measured locations $M_0, M_1, M_2, M_3$ (FIG. 2B). The weighted position error score is given by equation (40):

$$E^{pos} = \sum_{j=0}^{N-1} w_j^{adaptive,pos}(E_j - M_j)^2 \tag{40}$$

where N is the number of position transducers, and $w_j^{adaptive,pos}$ is an adaptive weighting for each position j.

The processor calculates a weighted orientation error score as a third term of the cost function. The score represents differences between orientations $E_j^{or}$ derived from locations of the position transducers, $E_0, E_1, E_2, E_3$, and orientations $M_j^{or}$ derived from the actual measured locations $M_0, M_1, M_2, M_3$. After deriving the two sets of orientations, the processor calculates the angular differences between the respective orientations using equation (41):

$$\{a_j, b_j\} = \text{Angles}((E_j^{or})^T \times M_j^{or}) \tag{41}$$

The processor generates an overall orientation error score according to equation (42):

$$E^{or} = \sum_{j=0}^{N-1} w_j^{adaptive,or}(a_j^2 + b_j^2) \tag{42}$$

where $w_j^{adaptive,or}$ is an adaptive weighting for each orientation.

Using the three terms above, the processor formulates a first cost function according to equation (43):

$$\text{Cost}(x_0, r_k, d) = \lambda^{int} E^{int} + \lambda^{pos} E^{pos} + \lambda^{or} E^{or} \tag{43}$$

where $\{\lambda^{int}, \lambda^{pos}, \lambda^{or}\}$ describe the relative importance of the deviation of probe 21 from its free shape compared to the position error and the orientation error.

In step 218 the cost function of equation (43) is minimized to determine best values of $E_0, E_1, E_2, E_3$, herein termed model-adjusted locations $\overrightarrow{ME}_j$ of the electrodes.

Second Cost Function

In step 219 the processor formulates a second cost function of the differences between the model-adjusted locations of equation (43) and the parameterized preliminary locations of equation (33). The second cost function is formulated according to equation (44):

$$C(P_A, \overrightarrow{ME}j, \overrightarrow{pfp}_i) = \|\overrightarrow{ME}j - \overrightarrow{pfp}_i\| \tag{44}$$

where $C(P_A, \overrightarrow{ME}j, \overrightarrow{pfp}_i)$ represents the cost function.

In step 220 the cost function of equation (44) is minimized, using all the locations of the electrodes on the catheter. Typically the minimization is performed using locations of the electrodes for sets of measurements for different locations of the catheter. Optionally, weights may be attached to the sets of measurements, typically according to a filter of the same general form as equation (4). The minimization is performed on expression (45):

$$\sum_L \|\hat{\overrightarrow{ME}}_j - \hat{\overrightarrow{pfp}}_i\| \tag{45}$$

where L is an index representing the different catheter locations.

The processor determines an optimal value of $P_A$ given by the minimization of expression (45) according to equation (46):

$$P_A = \underset{P_A}{\mathrm{ArgMin}}\left(\sum_L \left\|\hat{ME}_j - \hat{pfp}_i\right\|\right) \tag{46}$$

In step 222 the optimal value of $P_A$ determined by equation (46) is applied to the parameterized preliminary locations of equation (33), to give improved locations for the electrodes of the catheter. The processor typically uses the improved locations in presenting an image of the catheter on display 54.

In some embodiments, the weights described above with reference to step 220 may be determined so that the value of $P_A$ derived according to equation (46) is further optimized. Determination of the weights in this case may be by comparing results from equation (33) with another process for measuring locations of the electrodes, such as by using one or more sensors 22 in a probe similar to hybrid catheter 20 (FIGS. 1A and 1B). Alternatively or additionally, the locations of the electrodes may be found, and the weights determined, by operating the probe in a simulator where the electrodes are visible and/or accessible.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

We claim:

1. A method, comprising: receiving at a processor an input indicative of respective measured locations of a plurality of points disposed along a length of a probe inside a body of a subject, the probe having a predetermined shape; applying a model of known mechanical properties of the probe to the respective measured locations with respect to a plurality of shapes of the probe different from the predetermined shape; choosing a shape of the plurality of shapes and determining preliminary coordinates of the respective measured locations responsively to the chosen shape; minimizing differences between the respective measured locations and the preliminary coordinates; and generating corrected coordinates of the points along the length of the probe based on the minimized differences.

2. The method according to claim 1, wherein receiving the input comprises receiving inputs from a plurality of position transducers disposed along the length of the probe, and wherein each of the plurality of points corresponds to a respective location of a respective one of the plurality of position transducers.

3. The method according to claim 2, wherein the respective one position transducer is selected from a group consisting of an impedance measurement electrode, a single-axis magnetic sensor, a three-axis magnetic sensor, and an ultrasonic sensor.

4. The method according to claim 1, wherein the plurality of points comprises a plurality of investigation-electrodes disposed along the length of the probe, and wherein receiving the input indicative of the respective measured locations comprises: positioning body-electrodes in galvanic contact with the body of the subject; positioning a mapping-tool, having a mapping-electrode, in the body of the subject; generating a set of calibration-currents between the body-electrodes and the mapping-electrode at different positions in the body; deriving a relation between the set of the calibration-currents and the different positions; generating respective sets of investigation-tool-currents between the body-electrodes and the plurality of investigation-electrodes; and determining the respective measured locations in response to the relation and the set of investigation-tool-currents.

5. The method according to claim 4, wherein positioning the mapping-tool comprises tracking the mapping-tool at the different positions using a location-measuring system.

6. The method according to claim 4, wherein positioning the mapping-tool comprises positioning the mapping-tool in a plurality of regions in the body, and wherein deriving the relation comprises determining for each region a respective different region-relation between the set of the calibration-currents and the different positions.

7. The method according to claim 1, and comprising applying an adjustment parameter to the preliminary coordinates to formulate parameterized preliminary coordinates, wherein minimizing differences comprises computing differences between the measured locations and the parameterized preliminary coordinates so as to determine a value of the adjustment parameter, and wherein generating the corrected coordinates comprises applying the value of the adjustment parameter to the preliminary coordinates to evaluate the parameterized corrected coordinates.

8. Apparatus, comprising: a probe having a plurality of points disposed along a length thereof, the probe having a predetermined shape outside the body; and a processor which is configured to: receive an input indicative of respective measured locations of the plurality of the points inside a body of a subject, apply a model of known mechanical properties of the probe to the respective measured locations with respect to a plurality of shapes of the probe different from the predetermined shape, choose a shape of the plurality of shapes and determine preliminary coordinates of the respective measured locations responsively to the chosen shape, minimize differences between the respective measured locations and the preliminary coordinates, and generate corrected coordinates of the points along the length of the probe based on the minimized differences.

9. The apparatus according to claim 8, wherein receiving the input comprises receiving inputs from a plurality of position transducers disposed along the length of the probe, and wherein each of the plurality of points corresponds to a respective location of a respective one of the plurality of position transducers.

10. The apparatus according to claim 9, wherein the respective one position transducer is selected from a group consisting of an impedance measurement electrode, a single-axis magnetic sensor, a three-axis magnetic sensor, and an ultrasonic sensor.

11. The apparatus according to claim 8, wherein the plurality of points comprises a plurality of investigation-electrodes disposed along the length of the probe, and wherein the apparatus further comprises: body-electrodes configured to be positioned in galvanic contact with the body of the subject; a mapping-tool, having a mapping-electrode configured to be positioned in the body of the subject; and wherein the processor is further configured to generate a set of calibration-currents between the body-electrodes and the mapping-electrode at different positions in the body; derive a relation between the set of the calibration-currents and the different positions; generate respective sets of investigation-tool-currents between the body-electrodes and the plurality of investigation-electrodes; and determine the respective apparent locations in response to the relation and the set of investigation-tool-currents.

12. The apparatus according to claim 11, wherein positioning the mapping-tool comprises tracking the mapping-tool at the different positions using a location-measuring system.

13. The apparatus according to claim 11, wherein positioning the mapping-tool comprises positioning the mapping-tool in a plurality of regions in the body, and wherein deriving the relation comprises determining for each region a respective different relation between the set of the calibration-currents and the different positions.

14. The apparatus according to claim 8, wherein the processor is configured to apply an adjustment parameter to the preliminary coordinates to formulate parameterized preliminary coordinates, wherein minimizing differences comprises computing differences between the apparent locations and the parameterized preliminary coordinates so as to determine a value of the adjustment parameter, and wherein generating the corrected coordinates comprises applying the value of the adjustment parameter to the preliminary coordinates to evaluate the parameterized corrected coordinates.

15. A computer software product comprising a non-transitory computer-readable medium having computer program instructions recorded therein, which instructions, when read by a computer, cause the computer to: receive an input indicative of respective measured locations of a plurality of points disposed along a length of a probe inside a body of a subject, the probe having a predetermined shape, apply a model of known mechanical properties of the probe to the respective measured locations with respect to a plurality of shapes of the probe different from the predetermined shape; choose a shape of the plurality of shapes and determine preliminary coordinates of the respective measured locations responsively to the chosen shape; minimize differences between the respective measured locations and the preliminary coordinates; and generate corrected coordinates of the points along the length of the probe based on the minimized differences.

16. The product according to claim 15, wherein receiving the input comprises receiving inputs from a plurality of position transducers disposed along the length of the probe, and wherein each of the plurality of points corresponds to a respective location of a respective one of the plurality of position transducers.

17. The product according to claim 16, wherein the respective one position transducer is selected from a group consisting of an impedance measurement electrode, a single-axis magnetic sensor, a three-axis magnetic sensor, and an ultrasonic sensor.

18. The product according to claim 15, and wherein the instructions cause the computer to apply an adjustment parameter to the preliminary coordinates to formulate parameterized preliminary coordinates, wherein minimizing comprises computing differences between the apparent locations and the parameterized preliminary coordinates so as to determine a value of the adjustment parameter, and wherein generating the corrected coordinates comprises applying the value of the adjustment parameter to the preliminary coordinates to evaluate the parameterized corrected coordinates.

* * * * *